US009892232B2

(12) United States Patent
Feldman et al.

(10) Patent No.: US 9,892,232 B2
(45) Date of Patent: *Feb. 13, 2018

(54) SYSTEM FOR VENDING MEDICATIONS FROM A VENDING MACHINE IN ACCORDANCE WITH A DOSING SCHEDULE THAT IS DOWNLOADED AND PROGRAMMED INTO THE VENDING MACHINE FROM A REMOTELY LOCATED ELECTRONIC MEDICATION ADMINISTRATION RECORD

(71) Applicant: Medherent, LLC, Annapolis, MD (US)

(72) Inventors: Joel F. Feldman, Owings Mills, MD (US); Yeardley W. Green, Stevenson, MD (US); Stanley I. H. Feldman, Baltimore, MD (US); Jeffrey C. Sweeter, Minnetonka, MN (US)

(73) Assignee: Medherent, LLC, Annapolis, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/331,071

(22) Filed: Oct. 21, 2016

(65) Prior Publication Data

US 2017/0199966 A1 Jul. 13, 2017

Related U.S. Application Data

(63) Continuation of application No. 14/832,157, filed on Aug. 21, 2015, now Pat. No. 9,477,817, which is a (Continued)

(51) Int. Cl.
*G06F 19/00* (2018.01)
*G07F 17/00* (2006.01)
*A61J 7/04* (2006.01)

(52) U.S. Cl.
CPC .......... *G06F 19/322* (2013.01); *A61J 7/0418* (2015.05); *A61J 7/0454* (2015.05); *A61J 7/0463* (2015.05);
(Continued)

(58) Field of Classification Search
CPC .................................................. G07F 17/0092
(Continued)

(56) References Cited

U.S. PATENT DOCUMENTS 4,847,764 A 7/1989 Halvorson
6,505,095 B1 1/2003 Kolls
(Continued)

OTHER PUBLICATIONS

Office Action dated Feb. 9, 2017 in Canadian Patent Application No. 2,906,161, 8 pages.
(Continued)

*Primary Examiner* — Timothy R Waggoner
(74) *Attorney, Agent, or Firm* — Panitch Schwarze Belisario & Nadel LLP

(57) ABSTRACT

An automated method is provided for recording contents of medication packages vended from a plurality of vending machines in electronic records, such as an electronic medication administration record (eMAR), that store records for a plurality of patients who are associated with respective vending machines. A vending event causes the electronic record to be populated. The contents of the medication packages vended from the vending machines are recorded in electronic records without communicating patient names or vended medications in the electronic message sent from the vending machines.

8 Claims, 36 Drawing Sheets

Related U.S. Application Data continuation of application No. 13/847,710, filed on Mar. 20, 2013, now Pat. No. 9,117,010.

(60) Provisional application No. 61/794,777, filed on Mar. 15, 2013, provisional application No. 61/613,648, filed on Mar. 21, 2012.

(52) U.S. Cl.
CPC ........ *A61J 7/0481* (2013.01); *G06F 19/3462* (2013.01); *G07F 17/0092* (2013.01); *A61J 2200/30* (2013.01)

(58) Field of Classification Search
USPC .................................................. 700/231–244
See application file for complete search history.

(56) References Cited

U.S. PATENT DOCUMENTS

| | | | |
|---|---|---|---|
| 6,594,549 B2 | 7/2003 | Siegel | |
| 6,766,219 B1 | 7/2004 | Hasey | |
| 7,069,226 B1 | 6/2006 | Kleinfelter | |
| 7,264,136 B2 | 9/2007 | Willoughby et al. | |
| 7,574,377 B2 | 8/2009 | Carapelli | |
| 7,706,915 B2 | 4/2010 | Mohapatra et al. | |
| 7,963,201 B2 | 6/2011 | Willoughby et al. | |
| 8,019,471 B2 | 9/2011 | Bogash et al. | |
| 8,027,748 B2 | 9/2011 | Handfield et al. | |
| 8,090,472 B2 | 1/2012 | Schifman et al. | |
| 8,196,774 B1 * | 6/2012 | Clarke .................. | A61J 7/0409 221/13 |
| 8,467,897 B2 | 6/2013 | Holmes et al. | |
| 8,757,435 B2 | 6/2014 | Van Oort et al. | |
| 8,983,654 B2 | 3/2015 | Sugimoto | |
| 2001/0025208 A1 | 9/2001 | Bartur | |
| 2006/0200369 A1 | 9/2006 | Batch et al. | |
| 2009/0167531 A1 | 7/2009 | Ferguson | |
| 2009/0259486 A1 | 10/2009 | Burg et al. | |
| 2010/0114367 A1 | 5/2010 | Barrett et al. | |
| 2010/0168904 A1 | 7/2010 | Henderson et al. | |
| 2010/0305975 A1 | 12/2010 | Daya et al. | |
| 2010/0324936 A1 | 12/2010 | Vishnubhatla et al. | |
| 2011/0000170 A1 | 1/2011 | Burg et al. | |
| 2011/0202174 A1 * | 8/2011 | Bogash ............... | G06F 19/3462 700/225 |
| 2011/0251850 A1 | 10/2011 | Stephens | |
| 2015/0019009 A1 | 1/2015 | Feldman et al. | |

OTHER PUBLICATIONS

Product brochure for "PharmacySupport." CaraSolva, Inc., Boulder, Colorado, 2011, 2 pages.

Product brochure for "MedSupport®." CaraSolva, Inc., Boulder, Colorado, 2011, 2 pages.

Product brochure for "MedSupport® for Providers." CaraSolva, Inc., Boulder, Colorado, 2011, 2 pages.

Gene Ostendorf, "DEX and MDB: A Primer for Vendors." printout from web page: http://www.vendingmarketwatch.com/article/10272928/dex-and-mdb-a-primer-for-vendors, Feb. 7, 2008, 5 pages.

Michael L. Kasavana and Glenn Butler, "Vending Technology Revolution." printout from web page: http://www.vending.org/technology/Vending_Technology_Revolution.pdf, original publication date: 2010 (as per Internet Archive Wayback Machine records), 11 pages.

Wikipedia entry for "Medication Administration Record." printout from web page: http://en.wikipedia.org/wiki/Medication_Administration_Record, last modified date: Dec. 23, 2011, 2 pages.

Wikipedia entry for "Health Level 7." printout from: http://en.wikipedia.org/wiki/Health_Level_7, last modified date: Dec. 28, 2011, 11 pages.

Brochure for PointClickCare eMAR system. Printout from web page: https://www.pointclickcare.com/pccwebsite/pdfs/eMar_VicVillage.pdf, 2008, 2 pages.

"EVA Data Transfer Standard." European Vending Association, printout from web page: http://www.vending-europe.eu/_includes/print.php?lg=en&cmp_id=17&safe_mode=, printout date: Feb. 29, 2012, original posting date: unknown, 3 pages.

"Data Transfer Standard EVA DTS 6.1." European Vending Association, Apr. 2008, 16 pages.

Karla Miller et al. "Evaluation of medications removed from automated dispensing machines using the override function leading to multiple system changes," printout from web page: http://www.ahrq.gov/downloads/pub/advances2/vol4/Advances-Miller_93.pdf, original publication date: 2008 (as per Internet Archive Wayback Machine records), 7 pages.

Rajeev B. Patel, "Reduction in Medication Errors in Hospitals." printout from web page: http://www.cwru.edu/med/epidbio/mphp439/Reduction%20in%20Medication%20Errors%20in%20Hospitals.htm, Spring 2004, 11 pages.

PCT Invitation to Pay Additional Fees and Where Applicable, Protest Fees for PCT/US14/30316 dated Jan. 15, 2015, 3 pages.

"Notification of Transmittal of the International Search Report and the Written Opinion of the International Searching Authority . . . " and corresponding "Search History" document for PCT/US14/30316, dated Mar. 16, 2015, 26 pages.

International Preliminary Report on Patentability for PCT/US14/30316, dated Sep. 24, 2015, 12 pages.

JuGeon Pak and KeeHyun Park. "Construction of a smart medication dispenser with a high degree of scalability and remote manageability." Journal of Biomedicine and Biotechnology, 2012, 10 pages.

Office Action dated Aug. 11, 2016 in Canadian Patent Application No. 2,906,161, 8 pages.

* cited by examiner

PACKAGED PILL DISPENSER

4 COLUMNS
31 SELECTIONS

| IP address | Contents of Slot 1 (COL 1) | Contents of Slot 2 (COL 2) | Contents of Slot 3 (COL 3) |
|---|---|---|---|
| ABCDEF | 1 pill of MEDICINE A<br>1 pill of MEDICINE B<br>2 pills of MEDICINE C | 1 pill of MEDICINE D<br>1 pill of MEDICINE E | 1 pill of MEDICINE A<br>1 pill of MEDICINE B<br>2 pills of MEDICINE C |
| GHIJKL | 1 pill of MEDICINE M<br>2 pills of MEDICINE N | 1 pill of MEDICINE O<br>1 pill of MEDICINE P<br>1 pill of MEDICINE Q | 1 pill of MEDICINE M<br>2 pills of MEDICINE N |

Figure 3

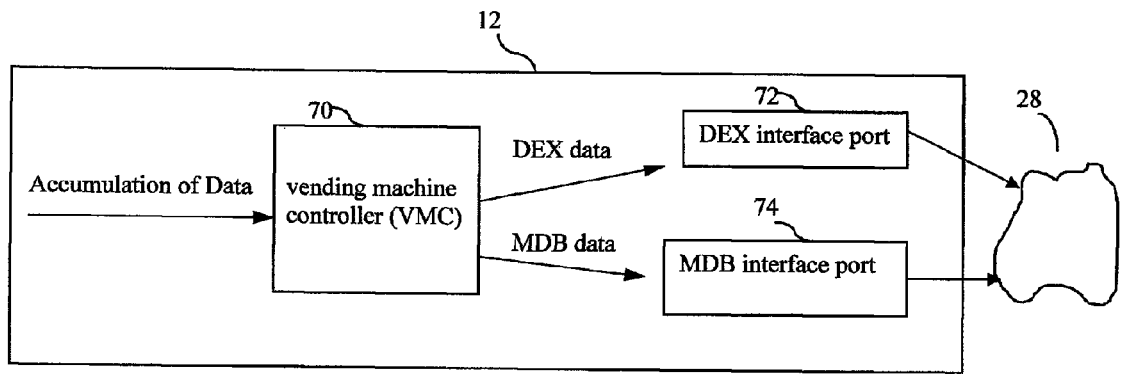

Figure 4

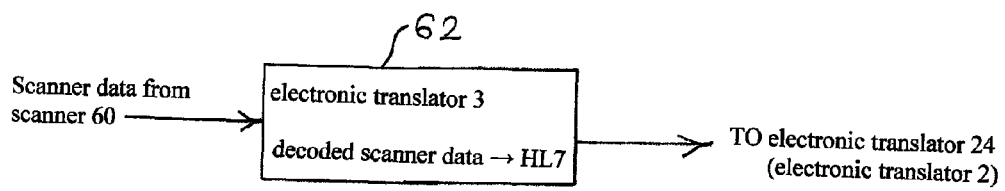

```
Administrator Detail         740
Description [                              ]
Current PIN [              ] 742            746
PIN [        ]          PIN Confirm [            ]
      744
[ Cancel Button ]  [ Delete Button ]  [ Ok Button ]
```

Figure 27

```
Consumer Detail    750        752        754
Last Name [          ]  SSN [    ]  DOB [    ]
Description [                                ] 756
PIN [        ]          PIN Confirm [            ]
     758                              760
[ Cancel Button ]         [ Register Button ]
```

Figure 39

Before

| | eMARs |
|---|---|
| 1 | Patient 123<br>:<br>8 AM Med A - Ready<br>8 AM Med B - Ready<br>8 AM Med C - Ready<br>12 PM Med A<br>12 PM Med C |
| 2 | Patient 456<br>:<br>7 AM Med F - Ready<br>9 AM Med B<br>9 AM Med C<br>11 AM Med A<br>11 AM Med C<br>: |

After

| | eMARs |
|---|---|
| 1 | Patient 123<br>:<br>8 AM Med A - Ready<br>8 AM Med B - Ready<br>8 AM Med C - Ready<br>12 PM Med A<br>12 PM Med C |
| 2 | Patient 456<br>:<br>7 AM Med F - Taken<br>9 AM Med B<br>9 AM Med C<br>11 AM Med A<br>11 AM Med C<br>: |

Patient Medication Table

| Patient ID | Dose schedule (time of prompts) | Dispensed meds (meds that are scheduled to be dispensed and which were previously placed into the vending machine) | Vended meds (populated upon detection of a vended event) | Actual time of vended event |
|---|---|---|---|---|
| 1234 | 8:00 AM | 1 pill of MEDICINE A<br>1 pill of MEDICINE B<br>2 pills of MEDICINE C | YES | 8:02 AM |
|  | 12:00 noon | 1 pill of MEDICINE D<br>1 pill of MEDICINE E |  |  |
|  | 8:00 PM | 1 pill of MEDICINE A<br>1 pill of MEDICINE B<br>2 pills of MEDICINE C |  |  |
| 5678 | 8:00 AM | 1 pill of MEDICINE M<br>2 pills of MEDICINE N | YES | 8:05 AM |
|  | 12:00 noon | 1 pill of MEDICINE O<br>1 pill of MEDICINE P<br>1 pill of MEDICINE Q |  |  |
|  | 8:00 PM | 1 pill of MEDICINE M<br>2 pills of MEDICINE N |  |  |

Figure 43

SYSTEM FOR VENDING MEDICATIONS FROM A VENDING MACHINE IN ACCORDANCE WITH A DOSING SCHEDULE THAT IS DOWNLOADED AND PROGRAMMED INTO THE VENDING MACHINE FROM A REMOTELY LOCATED ELECTRONIC MEDICATION ADMINISTRATION RECORD

CROSS REFERENCE TO RELATED APPLICATION

This application is a continuation of U.S. application Ser. No. 14/832,157 filed Aug. 21, 2015, which, in turn, is a continuation of U.S. application Ser. No. 13/847,710 filed Mar. 20, 2013, now U.S. Pat. No. 9,117,010, the entire disclosures of which are both incorporated by reference herein.

This application claims the benefit of U.S. Provisional Patent Application No. 61/613,648 filed Mar. 21, 2012, and U.S. Provisional Patent Application No. 61/794,777 filed Mar. 15, 2013, the entire disclosures of which are both incorporated by reference herein.

COPYRIGHT NOTICE AND AUTHORIZATION

Portions of the documentation in this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

Current medication dispensing devices, such as the devices described in U.S. Pat. No. 7,963,201 (Willoughby et al.), address many of the issues associated with medication adherence or medication compliance, which refers to the act of taking medications in a prescribed dosage, during a prescribed window of time at prescribed intervals. However, current devices still do not address many needs of the industry, particularly with respect to patient privacy issues. The present invention addresses this need.

SUMMARY OF THE INVENTION

An automated method is provided for recording contents of medication packages vended from a plurality of vending machines in electronic records, such as an electronic medication administration record (eMAR), that store records for a plurality of patients who are associated with respective vending machines. A vending event causes the electronic record to be populated. The contents of the medication packages vended from the vending machines are recorded in electronic records without communicating patient names or vended medications in the electronic message sent from the vending machines.

BRIEF DESCRIPTION OF DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. However, the invention is not limited to the precise arrangements and instrumentalities shown.

FIG. 3 shows a database table of the first implementation that is populated with data when a PMVD is loaded with medicine.

FIG. 4 shows a schematic block diagram of the first implementation illustrating how vending machine data within a PMVD may be communicated to an electronic network.

FIG. 5 shows an alternative embodiment of the first implementation wherein decoded scanner data from a scanner is converted to HL7 protocol compatible data.

FIGS. 20-32 show user interface display screens of a vending machine for use in one preferred embodiment of the second implementation.

FIG. 39 shows portions of an eMARs before and after the event posting in FIGS. 35-38.

FIG. 43 shows a patient medication table for use in one preferred embodiment of the second implementation.

DETAILED DESCRIPTION OF THE INVENTION

Certain terminology is used herein for convenience only and is not to be taken as a limitation on the present invention. For the purposes of explaining the present invention, specific embodiments will be described. These embodiments are exemplary only, and are not intended to limit the scope of the invention.

This patent application includes an Appendix having a file named appendix688372-1U4.txt, created on Oct. 11, 2016, and having a size of 17,879 bytes. The Appendix is incorporated by reference into the present patent application. One preferred embodiment of the present invention is implemented via the source code in the Appendix. The Appendix is subject to the "Copyright Notice and Authorization" stated above.

The present invention may be used to track the ingestion/administering/vending of single medicine packages or Multi-Unit Dose Packages or Multi-Unit Drug Packages (MUDPs). An MUDP contains one dosage of medicines that are prescribed for a specific treatment regimen. That is, there are a plurality of different medicines in an MUDP, and there may be one or pills of each medicine to obtain the desired dosage. All of the different medications in an MUDP packet are meant to be taken at the same time. MUDPs are typically created using specialized robotic machinery. However, the scope of the present invention includes MUDPs that are manually packaged in simple plastic packets or the like.

An MUDP typically includes a label that describes its contents, or it may include human or machine readable indicia (e.g., an ID number) that functions as a pointer in a database memory that stores its contents. The label may also include patient identifying information. The machine readable indicia may be a bar code or QR code that identifies the patient, date, and medication. The examples described below relate to MUDPs, but the scope of the present invention includes single medicines or packages that include only one medicine type per package.

Two example implementations of the present invention are described below.

I. Implementation 1

Figure 1:
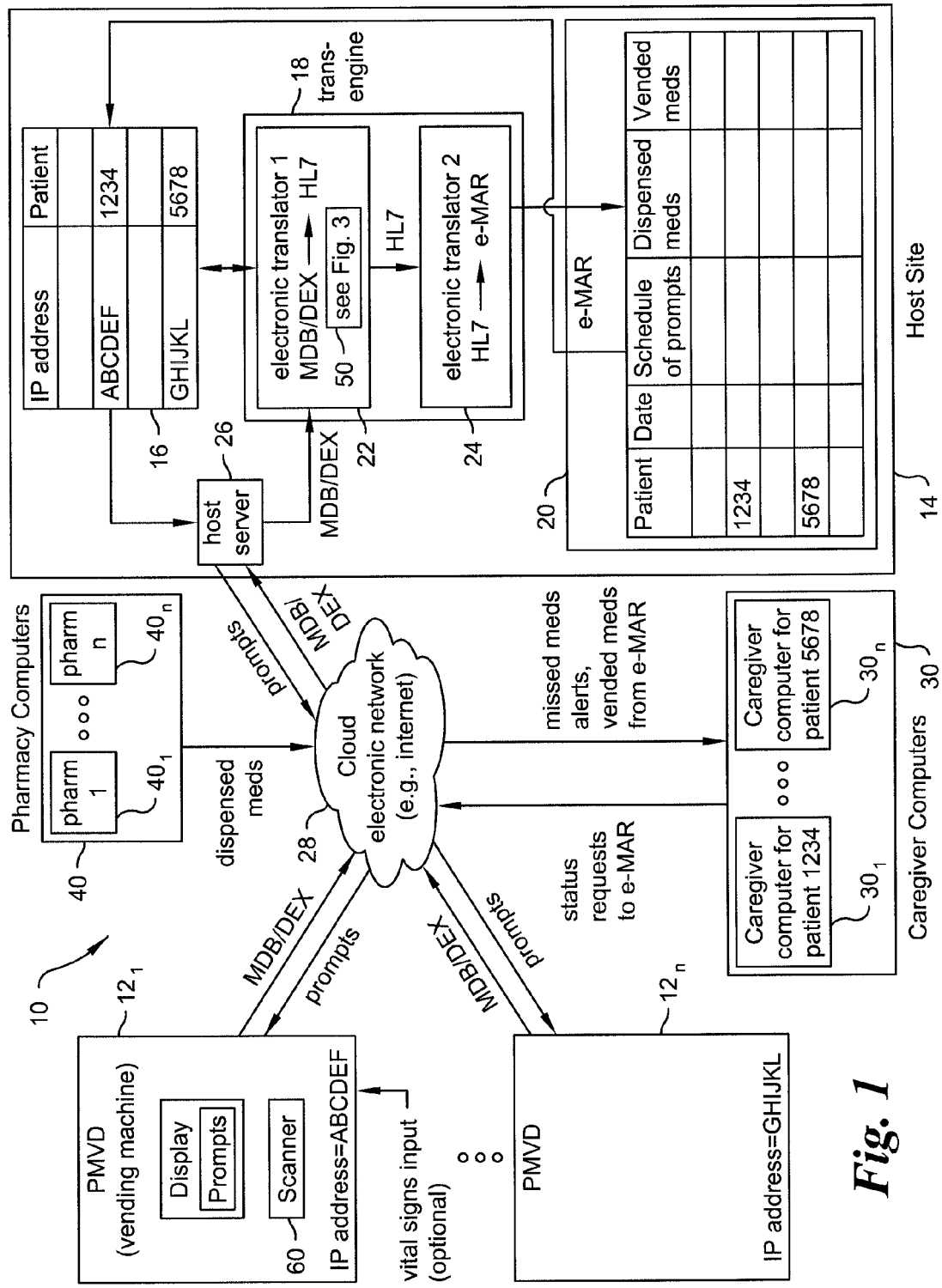
FIG. 1 is a schematic diagram of the system components of a first preferred implementation of the present invention.
Figure 2A:
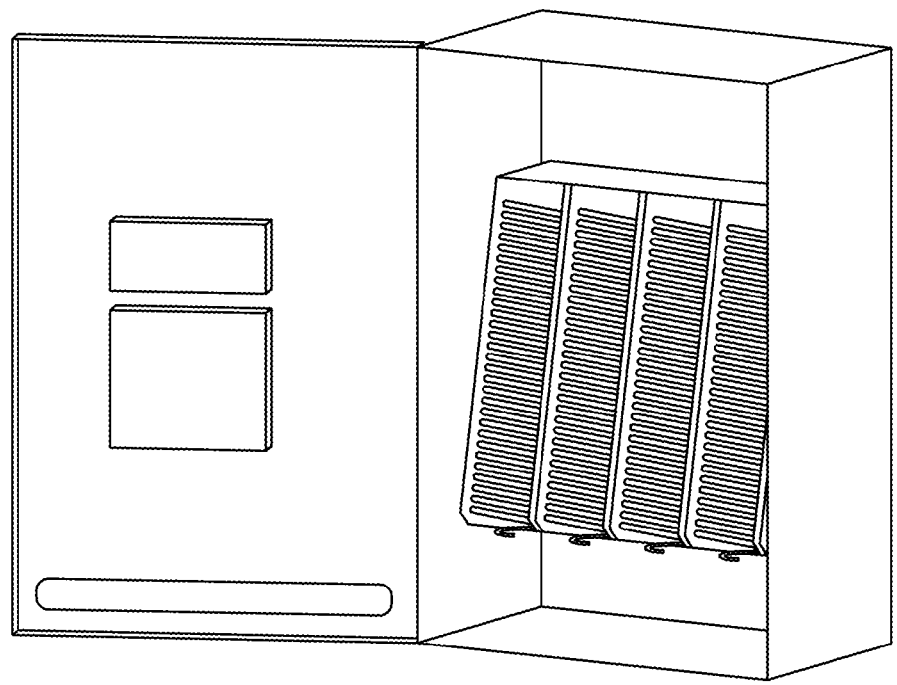
FIGS. 2a-2e show different views of a portable medication vending device (PMVD) that is suitable for use in the first implementation.
Figure 2B:
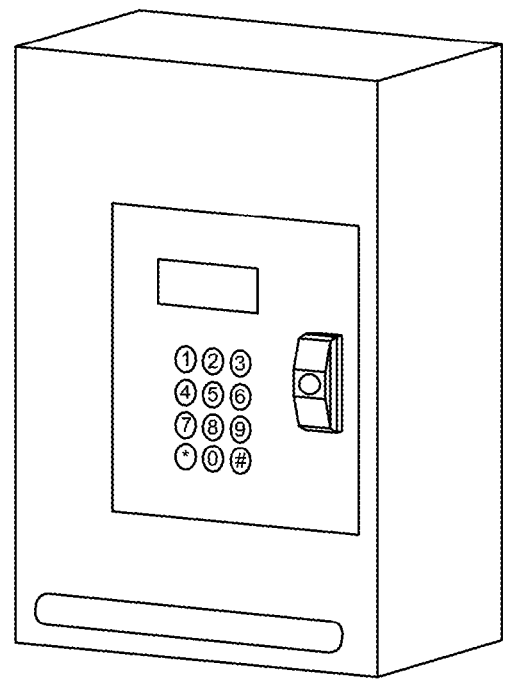
Figure 2C:
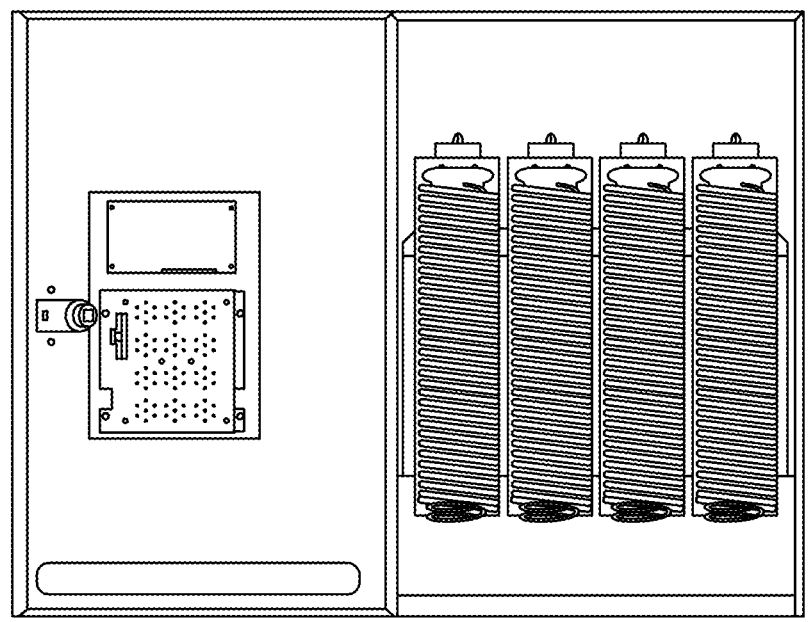
Figure 2D:
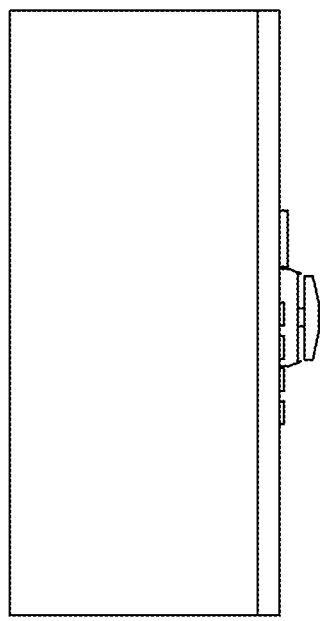
Figure 2E:
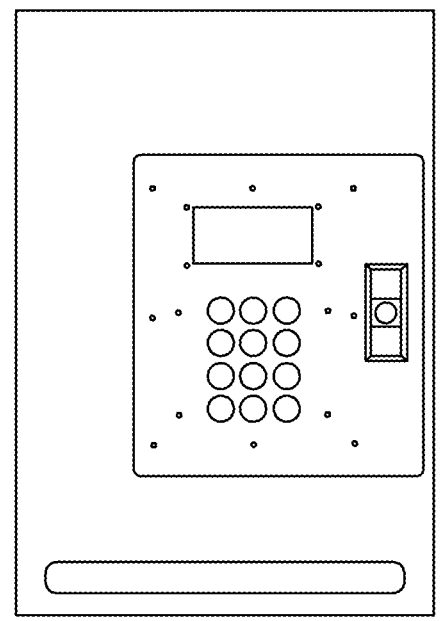

FIG. 1 is a schematic diagram of the system components of one preferred embodiment of the present invention. The overall system is designated as system 10 and includes at least the following five elements:

1. A network of portable medication vending devices (PMVDs) 12 for use by individual patients in a home environment, designated as $12_1$ through $12_n$. In a typical scenario, there is one PMVD 12 per patient, and thus there will typically be one PMVD 12 per home. The PMVDs 12 may also be used in other environments, such as nursing homes or hospitals, wherein each resident or patient may have its own PMVD 12 in his or her respective housing unit or hospital room. The word "patient" is used herein to designate the individual whose medications are present in the PMVD 12. The word "user" is used herein to designate an individual who physically interacts with the PMVD 12. In most instances, the patient will be the user, but a caregiver may also be a user, especially if the patient is unable to operate the PMVD 12. Each PMVD 12 has a unique IP address. It is well-known in the art to assign unique IP addresses to physical devices, such as conventional vending machines, and any suitable assignment scheme may be used.

2. A host site 14 that includes one or more databases 16, an electronic translation engine 18, and an electronic medication administration record (e-MAR or eMAR) 20. The one or more databases 16 includes a table that associates the IP address of a PMVD 12 to a specific patient so that any data received from the PMVD 12 will be associated with the correct patient, and so that any data that needs to be sent to the patient will be routed to the correct PMVD 12.

The electronic translation engine 18 has the overall function of receiving vending machine data in a conventional vending machine data format, such as DEX data or MDB data (described in more detail below) and converting the data to a format that can be directly input into the eMAR 20. The IP address/patient identity information in the database 16 is used to identify which patient the eMAR data belongs to so that the appropriate patient record within the eMAR 20 can be updated. More specifically, the electronic translation engine 18 includes a first electronic translator 22 and a second electronic translator 24. The first electronic translator 22 performs a conversion of the DEX data or MDB data into HL7 data. (HL7 is an abbreviation of Health Level Seven, which is a standard for exchanging information between medical applications. HL7 defines a format for the transmission of health-related information.) The second electronic translator 24 converts the HL7 data into eMAR data. There is no standard eMAR format, and it varies from system to system. However, a typical eMAR will include patient ID information (e.g., name, medical record number) and medication details (drug name, dosage strength, frequency to be taken, date/time that each medication was taken).

The first electronic translator 22 also includes database 50 which is described below with respect to FIG. 3.

In an alternative embodiment, there is only one electronic translator which directly converts the DEX data or MDB data into eMAR data. However, the two-step conversion process has enhanced versatility because the HL7 data may be used for many other purposes, such as for communications with other healthcare systems that may need to know about patient medication events. Also, electronic translators for converting HL7 data into eMAR data are well-known in the prior art. Thus, the software for the overall conversion process may be simplified by performing the MDB/DEX to HL7 conversion by the first electronic translator 22, and then adding a conventional second electronic translator 24 to the output of the first electronic translator 22.

In one preferred embodiment, the eMAR 20 includes data fields for patient ID, date, schedule of prompts, and vended medications. The date field is shown in simplified form in FIG. 1. The actual eMAR 20 includes more granular date information. The schedule of prompts field stores dates/times that a prompting signal should be sent to the patient's PMVD to prompt the patient that it is time to take medication. The vended medications field stores dates/times that a signal is received from a PMVD 12 indicating that a vending event occurred. The vended medications field is also shown in simplified form in FIG. 1. The actual eMAR 20 includes more granular vended medications data, including exactly which medications were taken at the date/time that a signal is received from a PMVD 12 indicating that a vending event occurred, as will be discussed in more detail below.

The patient ID field preferably includes the patient's medical record number, either as the entire field or part of the field. If the patient's medical record number is not contained within the patient ID field, another database table will need to be maintained by the host site 14 so that the eMAR can be properly populated.

A conventional paper-based medication administration record (MAR) functions as a recording of the medications taken by a patient, typically during the patient's stay in a health care facility. A health care professional typically signs or initials the MAR upon witnessing or administering the medication. In an eMAR, the signature or initials are electronically recorded, but the concept is the same as a paper-based MAR. These types of MARs have a field for recording "dispensed medications."

In the present invention, a "dispensed medications" field is optional. However, the eMAR 20 needs to include a "vended medications" field. As discussed in more detail below, there are two steps involved in the medication lifecycle. The first step in the lifecycle is a dispensing step which occurs when a pharmacist or similarly qualified individual fills the PMVD 12 with prescribed medications. This step is conventionally referred to as "medication dispensing," wherein specific medication(s) are delivered to a patient in fulfillment of a prescription. Typically, the medications are physically handed to the patient, but in the present invention, the medications are loaded into the PMVD 12, thereby completing the dispensing step. The second step in the lifecycle is a vending step wherein the PMVD 12 releases the previously dispensed medications to the patient. In a conventional vending machine, the release of a product from a vending machine is typically referred to as a dispensing event, but in the context of the present invention, it is referred to as a vending event, because the dispensing event occurred when the PMVD 12 was loaded with the medications.

Referring again to a conventional eMAR, the step of administering medications to a patient is typically considered to be the dispensing event, and is the only event recorded in a conventional eMAR. That is, a conventional eMAR typically does not capture the event that occurs when a hospital pharmacy or the like releases patient medications to the health care professional for subsequent delivery to, and ingestion by, the patient. Of course, the pharmacy may capture this event for its own inventory records, and for patient billing purposes. Consider, for example, a typical hospital scenario wherein a hospital-based pill dispensing cart is filled at a hospital pharmacy, and is then moved from room to room to dispense the medications to the patients, the conventional eMAR being populated with data as the patients receive their medications.

The "vended medications" field in the eMAR 20 thus defines a different paradigm than the conventional field of an eMAR that records dispensed medications. However, the "dispensed medications" field of a conventional eMAR and the "vended medications" field of eMAR 20 relate to the same patient medication ingestion event (i.e., when the patient is presumed to have ingested the medications, and what medications are presumed to have been ingested). Accordingly, when the first electronic translator 22 receives a signal from a PMVD 12 that a vending event has occurred, the outputted HL7 signal corresponds with a medication ingesting event so that the "vended medications" field of the eMAR 20 can be properly populated.

The eMAR 20 may optionally include a "dispensed medications" field for recording when a pharmacy dispensed the medications and what medications were dispensed. For example, a pharmacy computer 40 may send data HL7 data to the second electronic translator 24 when a prescription is filled, or the pharmacy computer may send the data directly to the eMAR in a form that the eMAR can accept. Furthermore, the schedule of prompts stored in the eMAR may be set by the pharmacy computer based on the prescription.

The eMAR 20 also includes a field (not shown) that contains contact information for entities who should be contacted if a medication dose is missed, such as a physician, caregiver, or family member.

The host site 14 also includes a host server 26 (host computer 26) for facilitating communications into and out of the host site 14.

While only one eMAR 20 is shown in FIG. 1, there may be a plurality of eMARs 20, each eMAR storing records for different patients. Thus, the host server 26 may need to determine which eMAR the incoming vending event data needs to be routed to. Alternatively, there may be a single eMAR 20, which, in turn, populates a replicated set of patient data at a plurality of different remotely located eMARs that store records for different patients.

In an alternative embodiment, the eMAR 20 is substituted by an electronic record that provides similar functionality as an eMAR, such as an electronic medication chart or electronic drug chart which may be separate from, or part of, an electronic medical record, and which can directly or indirectly (via an additional electronic translator) accept eMAR data. The eMAR 20 is thus one specific type of the electronic record. If the eMAR 20 is substituted by an electronic record, there may be a plurality of such electronic records, each electronic record storing records for different patients, in the same manner as described above with respect to the multiple eMAR 20 embodiment.

3. An electronic network 28, such as the Internet, allows for communications between the PMVDs 12 and the host server 26.

4. A plurality of caregiver computers 30, designated as $30_1$ through $30_n$, that allow patient caregivers to query the e-MAR 20 and receive alerts if any medications are not vended in accordance with the schedule. The caregiver computer 30 may be any conventional computer with a browser-based user interface. The user interface is preferably accessed via a cloud-based software-as-a-service (SAS) model, so that no special software needs to be present in the caregiver computer 30 to allow for its use. A userid and password is associated with each patient so that the caregiver is given access only to the patient records in the eMAR that match the appropriate patient. The caregiver may be a patient's medical care provider, or the caregiver may be a family or friend. Thus, as used herein, the caregiver includes persons who are monitoring the patient, regardless of whether they are actually rendering formal medical care to the patient.

5. A plurality of pharmacy computers 40, designated as $40_1$ through $40_n$, that allow pharmacists to communicate the contents of PMVDs 12 that they fill (dispense) with medications to the database 50 in the first electronic translator 22 of the host site 14. The pharmacy computer 50 may be any conventional computer with a browser-based user interface. The user interface is preferably accessed via a cloud-based software-as-a-service (SAS) model, so that no special software needs to be present in the pharmacy computer 30 to allow for its use.

PMVD 12

Figure 11:
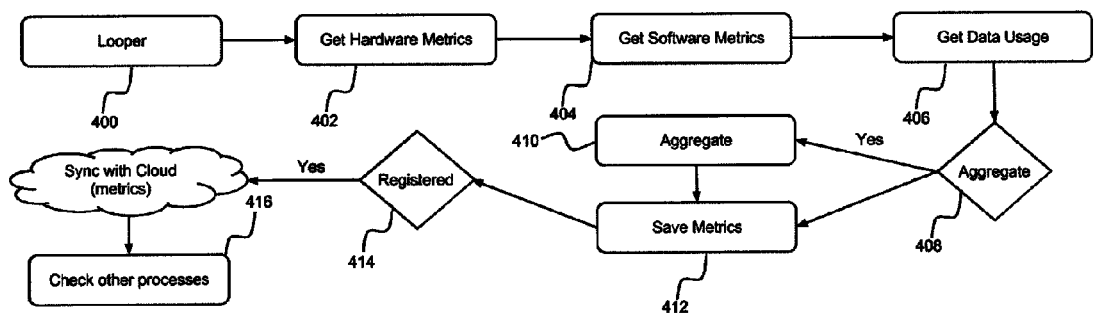

The PMVD 12 may have a vending mechanism that is similar to snack food-type vending machines, except in a much smaller form factor. In one well-known type of vending machine, the goods to be vended are placed in slots or compartments formed from turns of helical coils. The goods rest on a shelf disposed parallel to the helical coil. Each of the helical coils is connected to a motor that, upon operation of the push-button panel that selects the goods, causes rotation of the helical coil about a longitudinal extension axis. This causes the goods to move forward in the turns while resting on the shelf. As the goods reach the final end of the helical coil, they are pushed beyond an end edge of the shelf and drop into a lower portion of the machine, such as a hopper where the goods can be retrieved. One example of this type of vending machine is shown in U.S. Pat. No. 8,052,010 (Borra), which is incorporated by reference herein. The helical coils can also be arranged vertically, so no shelf would be necessary. In the present invention, the goods are MUDPs which are loaded into the PMVD 12. FIGS. 10 and 11 of U.S. Pat. No. 7,963,201 (Willoughby et al.) shows a similar idea for dispensing MUDPs using vertically arranged helical coils. U.S. Pat. No. 7,963,201 is incorporated herein in its entirety.

In one example, the PMVD 12 may have three vending column or slots, one for vending a morning MUDP, one for vending a noon MUDP, and one for vending an evening MUDP. The PMVD 12 is preferably loaded at a pharmacist who records in a database record for the patient which MUDPs were placed in each of the compartments defined by the vending columns or slots.

The individual slots or compartments formed from turns of helical coils are not to be confused with the vending columns, which are also referred to in the vending industry as "slots." To avoid confusion, the individual slots or compartments are referred to hereafter as "compartments."

FIGS. 2a-2e show different views of a PMVD 12 that is suitable for use in the present invention. The PMVD 12 has four columns (slots), each column (slot) having a plurality of individual compartments for holding MUDPs. There is preferably one MUDP placed in each compartment. For purposes of illustration, the example below uses three columns, one for vending the morning MUDP, one for vending the noon MUDP, and one for vending the evening MUDP. The PMVD 12 shown in FIGS. 2a-2e may be used, wherein only three of the four columns are filled. The PMVD 12 uses vertical columns. However, other physical embodiments are within the scope of the present invention. An alternative embodiment may be a stack of rotatable trays, each tray being equivalent to one of the respective columns in the PMVD 12 of FIGS. 2a-2e, wherein each tray has a plurality of defined individual compartments placed around each respective tray for placing the MUDPs to be vended.

The compartments may be physical, as in the example of FIGS. 2a-2e, or they may be virtual, wherein the compartments are defined by predetermined locations within a column or tray.

FIG. 3 shows a database table 50 that is populated with data, preferably entered by a pharmacist, when a PMVD 12 is loaded with medicine. The IP address of the PMVD 12 must be identified. The contents of each slot (column) is also identified. In the example of FIGS. 2a-2e, the PMVD 12 having IP address ABCDEF is loaded with a one month supply of medicine, as follows:

Slot 1 (COL 1): 31 MUDPs, each MUDP including 1 pill of medicine A, 1 pill of medicine B, and 2 pills of medicine C.

Slot 2 (COL 2): 31 MUDPs, each MUDP including 1 pill of medicine D, 1 pill of medicine E.

Slot 3 (COL 3): 31 MUDPs, each MUDP including 1 pill of medicine A, 1 pill of medicine B, and 2 pills of medicine C.

FIG. 3 also shows the contents of a PMVD 12 having IP address GHIJK, which is for a patient that is on a completely different medication regimen than the other patient.

When a vending event occurs, such as the vending of an MUDP from slot 1 (column 1) of the PMVD 12 having IP address ABCDEF, the vending event is received by the first electronic translator 22, which accesses database tables 16 and 50, and can determine which patient the vending event relates to, and which medicines were vended. In this example, if the vending event occurred in the morning, the medicines will be 1 pill of medicine A, 1 pill of medicine B, and 2 pills of medicine C, dispensed to patient 1234. This data may then be converted into an HL7 format, and subsequently converted into eMAR data for populating the "vended medications" field of eMAR 20 for patient 1234. In this manner, one vending event may result in the recordation of multiple medications having been vended. Thus, multiple records may be populated in the eMAR 20 (one record for each medicine).

Vending Events

Vending machine data is preferably communicated using a conventional vending machine data format, such as DEX data or MDB data. DEX (Data Exchange) is a format for collecting audit and event data from vending machines. MDB (multidrop bus) is an internal communication protocol to allow subparts of a vending machine to properly interface with a vending machine controller (VMC). FIGS. 9A-9C of U.S. Pat. No. 6,505,095 (Kolls) illustrate the use of a VMC with MDB and DEX, and the corresponding description of these figures explains many of the details for formatting vending machine data for external communication and use. U.S. Pat. No. 6,505,095 (Kolls) is incorporated herein by reference in its entirety. Furthermore, DEX and MDB each have published standards that describe, in detail, how they function.

For example, Chapter 4.7 of a document entitled Data Transfer Standard EVA DTS 6.1, published by the European Vending Association in April 2008, which is part of the DEX standard, provides a DEX Data Transfer Example on page 13 that includes at least the following information:

1. The ID of the vending machine that is communicating its vending activity

2. All vending activity that occurred since the last interval data reset, by column (there are five columns in this example, designated COL1 through COL 5)

This example shows a typical DEX data transfer between a Data Carrier and Vending Machine Device. The Data Carrier is a device for collecting data from the Vending Machine Device and transmitting the data remotely.

The current standards for MDB is Version 4.0 published April 2009 by National Automatic Merchandising Association (NAMA).

FIG. 4 shows a schematic block diagram illustrating how vending machine data within a PMVD 12 may be communicated to the electronic network 28. An accumulation of data is received by a vending machine controller (VMC) 70 which electronically produces DEX data and/or MDB data, which is communicated to DEX interface port 72 and/or MDB interface port 74, which, in turn, communicate such data to the electronic network 28. Thus, in one preferred embodiment, the vending machine controller data exchange (DEX) interface communicates vending events to the electronic network 28. In another preferred embodiment, the vending machine controller multi-drop bus (MDB) interface communicates vending events to the electronic network 28.

Regardless of which machine data format is used, the outgoing messages will include at least (1) the IP address of the PMVD 12, the slot/column of the vending event, and (3) the time of vending.

HL7

As discussed above, HL7 defines a format for the transmission of health-related information. HL7 has published standards and HL7 3 is the current standard. Additional information regarding HL7 is available at http://www.hl7.org/.

HL7 communicates via HL7 messages which are made up of a sequence of messages having segments, fields, and message types.

Admissions Message Segments include a Patient Identification Segment (PID). The PID includes one or more forms of patient ID numbers, and a patient medical record number.

Pharmacy order segments include complete information regarding medication types, dosages and dispensing schedules. While these messages are conventionally meant to be used in conjunction with pharmacy orders, not for representing vended medications, HL7 messages may be created that contain pharmacy orders, but which are used in the present system to represent vended medications.

By using HL7 messages having Admissions Message Segments and Pharmacy order segments and the data in databases 16 and 50, the first electronic translator 22 may create HL7 messages that fully describe which patient received vended medications and which medications were vended.

Additional Considerations

FIGS. 2a-2e show one preferred embodiment of a PMVD 12 that vends products placed in slots formed from a helical coil. However, the PMVD 12 may be constructed in a manner similar to any other type of conventional vending machine that releases products upon appropriate triggers. Other physical structures such as rollers may be used to move and release the MUDPs from the PMVD 12.

As shown in FIGS. 2a-2e, the PMVD 12 preferably includes at least one electronic display screen to display text and/or graphics, at least one speaker for delivering audio, and at least one button, keypad, or swipe card device that enables the patient to activate the PMVD 12 so as to initiate a vending event. The text and/or graphics and speaker are used to prompt the patient to initiate a vending event in accordance with the schedule of prompts stored in the eMAR 20. In the example described above, medication must be taken three times per day, such as at 8:00 am, 12 noon, and 6:00 pm.

The PMVD 12 has an internal clock and at least one reliable power source, and preferably has a backup power source which can sustain functionality of the PMVD 12 for extended periods of time so as to ensure the continuity of care. For example, the PMVD 12 may receive power from a standard electrical outlet and may include an automatically rechargeable backup battery that automatically takes over power functions upon disruption of electrical power, and automatically reverts to standby mode upon resumption of power. Caregivers, pharmacies, and physicians may also be provided with the ability to remotely turn off all power to the PMVD 12.

As discussed above, the PMVD 12 may communicate with the host server 26 via an electronic network 28, such as the Internet. The communication may be wired or wireless. The wireless communication may be any conventional form of such communication, including short range wireless signals, such as Bluetooth® signals.

The PMVD 12 may have a conventional full keypad that may be used to enter security code (e.g., a Personal Identification Numbers (PIN)) for initiating a vending event, or there may be a simple, dedicated key, such as the "#" or "*" key that must be pressed for initiating the vending event. The keypad may also be used to input information such as patient blood pressure readings, blood glucose levels, and the like. In this manner, the PMVD 12 may also be used to prompt a patient to take and record their blood pressure, blood glucose levels, and other similar vital signs. This can allow a physician or other healthcare professional to diagnose conditions remotely and in real-time. The PMVD 12 can also be programmed to have different prompts depending on the vital sign measurement. For example, if a patient enters a glucose reading above a certain level, the PMVD 12 may announce, "Take your diabetes medicine now," or "Call your physician immediately." If the medicine is insulin, the PMVD 12 may also be programmed to announce, "Your insulin is in refrigerator."

The PMVD 12 may have the ability to read identification (ID) cards or other similar devices belonging to patients and caregivers. When a patient (and possibly the caregiver) enters a PIN or swipes their user ID card, the PMVD 12 may ask, "Do you want the 8:00 AM meds?" Also, different user IDs, ID devices, and security settings may allow for different levels of functionality. For example, a caregiver's security setting may allow the user to vend missed doses. However, the patient's security setting may not allow the user to vend missed doses.

After the PMVD 12 receives a prompt and communicates the prompt (visually and/or audibly), the PMVD 12 may also periodically communicate reminders (visually and/or audibly) until the patient initiates a vending event. The reminders will continue for whatever preprogrammed period of time is set by the pharmacist or other authorized entity. The reminders will stop when it is determined that the patient should no longer take the missed dose. After the reminders are stopped, the patient will be locked out of initiating a vending event until the next scheduled vending event occurs. When the next vending event occurs, the patient will receive the next vended MUDP from a different vending slot in the example discussed above. The PMVD 12 may also be programmed to allow a physician to override the lockout so that the patient may take a missed dose past the lock out time if the physician deems that it is safe to do so.

As discussed above, a caregiver may log into the eMAR 20 and view the vending medications, noting any missed medications. The PMVD 12 and/or the eMAR 20 may also electronically send medication alerts to the patient caregiver via email, SMS (text messages), or automated phone messages.

The vending example discussed above provides a PMVD 12 that can accept 31 MUDPs to be loaded into three vending slots to allow for three vending events per day. However, the PMVD 12 may have any suitable number of vending slots to accommodate more or less than three vending events per day. To increase the versatility of the PMVD 12, it may have five vending slots, and anywhere from one to all five of the slots may be filled for a particular patient's needs. The PMVD 12 may also be filled with a 32 day supply of medication. The extra day(s) would be a safeguard if a patient spills of drops their medications.

If all of the MUDPs contain the same medication, there may be more flexibility in the vending process. For example, the MUDP can be vended from any available slot that is not empty since there would be no need to associate different vending slots with different time periods.

In an alternative embodiment, the PMVD 12 has a waste bin that received missed doses. Thus, after the predetermined period of time in which the reminder message is stopped, the missed dose is vended into the waste bin, instead of being left in the vending region, such as the slots of the helical coils.

The PMVD 12 may optionally include a scanner 60 that can read a bar code or QR code printed on an MUDP as the MUDP is vended. This information may act as a backup to the process described above wherein the databases 16 and 50 are used to correlate a vending event to the appropriate information that is needed to populate the eMAR 20. Such a scanner may be required to comply with some health care regulations.

FIG. 5 shows an alternative embodiment of the present invention wherein the decoded scanner data from the scanner 60 is converted to HL7 protocol compatible data in a third electronic translator 62 (labeled as "electronic translator 3"), which becomes the input data for the second electronic translator 24 of FIG. 1. In this embodiment, the database 50 is not required to resolve the data because the scanner data provides the same detailed information regarding the contents of the MUDP that would have otherwise been retrieved from the database 50. Furthermore, if the scanner data includes patient ID data retrieved from the MUDP, the database 16 may also not be required to resolve the data to a particular patient's records in the e-MAR 20. However, if the patient ID data retrieved from the MUDP is not in the same format as the patient ID data in the e-MAR 20, another database (not shown) will be needed to convert the patient ID retrieved from the MUDP to the patient ID format used in the e-MAR 20.

Medications such as Tylenol® which are taken only when needed (i.e., PRN meds), and not taken on a regular schedule, are kept outside of PMVD 12. PRN meds may be packaged in blister packs so they can be easily counted, tracked and billed. Although PRN meds may be kept outside of the PMVD 12, the PMVD 12 can still play an instructing role by prompting a patient when to take a non-packaged medication. For example, the PMVD 12 can have an audio prompt such as, "If you are experiencing pain, you should take your Tylenol now." The pharmacy can input information into the PMVD 12 which shows that a PRN med can be taken every six hours. Then, the PMVD 12 will prompt the patient (e.g., by announcement or text message) every 6 hours.

There is preferably a "double lock" system for Controlled Dangerous Substances (CDS). For example, when it is time for a patient to take a CDS, the PMVD 12 will dispense an empty package labeled, "You need to take Ritalin®." The Ritalin (a CDS) is kept in a safe place outside of PMVD 12 so that no one is tempted to tamper with the PMVD 12 to gain access to a CDS.

Insurance companies do not normally pay for remote monitoring devices. For example, pharmacies are not reimbursed for blood glucose monitors which have the ability to report back to a central database. However, if the PMVD 12 is tied to an eMAR, it can be a very effective tool to assist doctors in inexpensively improving patient health and safety, and insurance companies may pay for this functionality. Consider the following examples:

EXAMPLE 1

A physician can see their patient's blood glucose readings, when the patient took insulin, and how much insulin was taken.

EXAMPLE 2

A psychotic patient gets arrested and misses his medications for two days. The patient's physician and caregivers are notified of the missed medications immediately after each missed dose.

In one preferred embodiment, an automated method is provided for recording contents of medication packages vended from a plurality of vending machines in an electronic record, such as an eMAR, that stores records for a plurality of patients who are associated with respective vending machines. The electronic record includes (i) a patient ID field, (ii) a vended medications field, and (iii) time of medication vending, the vending machine including (i) an IP address, (ii) a vending machine controller (VMC), (iii) one or more vending slots or columns, each slot or column holding a medication package to be vended, and (iv) a vending machine data format interface connected to an electronic network for communicating vending machine data, the vending machine's IP address, and the time of vending events. The vending machine data includes the vending slot or column that medications were vended from. In use, the method operates as follows:

1. A first database is provided that stores the IP addresses of the plurality of vending machines and the patient ID's of the respective vending machines. A second database is provided that stores IP addresses of the plurality of vending machines and the contents of the medication packages in each of the slots or columns of the respective vending machines.
2. A vending event is initiated at the vending machine. The vending event is captured by the VMC and communicated to the electronic network as vending machine data via the vending machine data format interface.
3. The vending machine data, the vending machine's IP address, and the time of vending events is received at a translation engine.
4. The vending machine data is converted into HL7 protocol compatible data by the translation engine and by using the data in the first and second databases. The HL7 protocol compatible data includes one or more HL7 compatible transaction messages that includes (i) the patient ID, (ii) the vended medication, and (iii) the time of the vending event.
5. The HL7 compatible transaction messages are then converted by the translation engine into electronic medication administration record (eMAR) data.
6. The electronic record is populated with the eMAR data for each of the vending events. The populated data includes for each patient, the vended medications and the time of the vending event.

In one preferred embodiment, there are a plurality of different slots or columns in the vending machine, and each slot or column contains medication packages with different medication contents.

In one preferred embodiment, the medications are vended in multi-unit dose packages (MUDPs), the contents of each MUDP being stored in the second database. A single vending event thereby causes the electronic record to record that a plurality of medications were vended.

In one preferred embodiment, the vending machine slots or columns are filled by a pharmacy during a medication dispensing process, and the pharmacy electronically populates the second database with the contents of the medication packages in each of the slots or columns of the respective vending machines.

In one preferred embodiment, the vending machine data format interface is a data exchange (DEX) interface, and the vending machine data is DEX data. In another preferred embodiment, the vending machine data format interface is a multi-drop bus (MDB) interface, and the vending machine data is MDB data.

End of Details of Implementation 1

II. Implementation 2

This implementation is described in the context of an integration of products/services from a plurality of different entities (vendors/companies). This implementation is not limited to this particular combination of entities. Furthermore, this implementation may alternatively be performed using products/services from the same entity. The entities are identified below:

Medherent: a medication adherence system, also referred to herein as a "medication administration computer."

CaraSolva Inc. (CaraSolva): CaraSolva, located in Boulder, Colo., licenses web-based software designed to automate and simplify the daily tasks performed by nurses and professional caregivers.

MedSupport®: MedSupport is CaraSolva's software module for scheduling of medications and the administration of medication. MedSupport provides a compliant eMAR. In addition, this module along with a pharmacy interface, allows prescriptions to automatically schedule into MedSupport®.

Med Pass outcome (Medpass event): This is a data element used in MedSupport. Med Pass outcomes are electronically recorded on the MedSupport eMAR.

Vended Medication Event Controller

Technical Processes and Entities

Figure 6A:
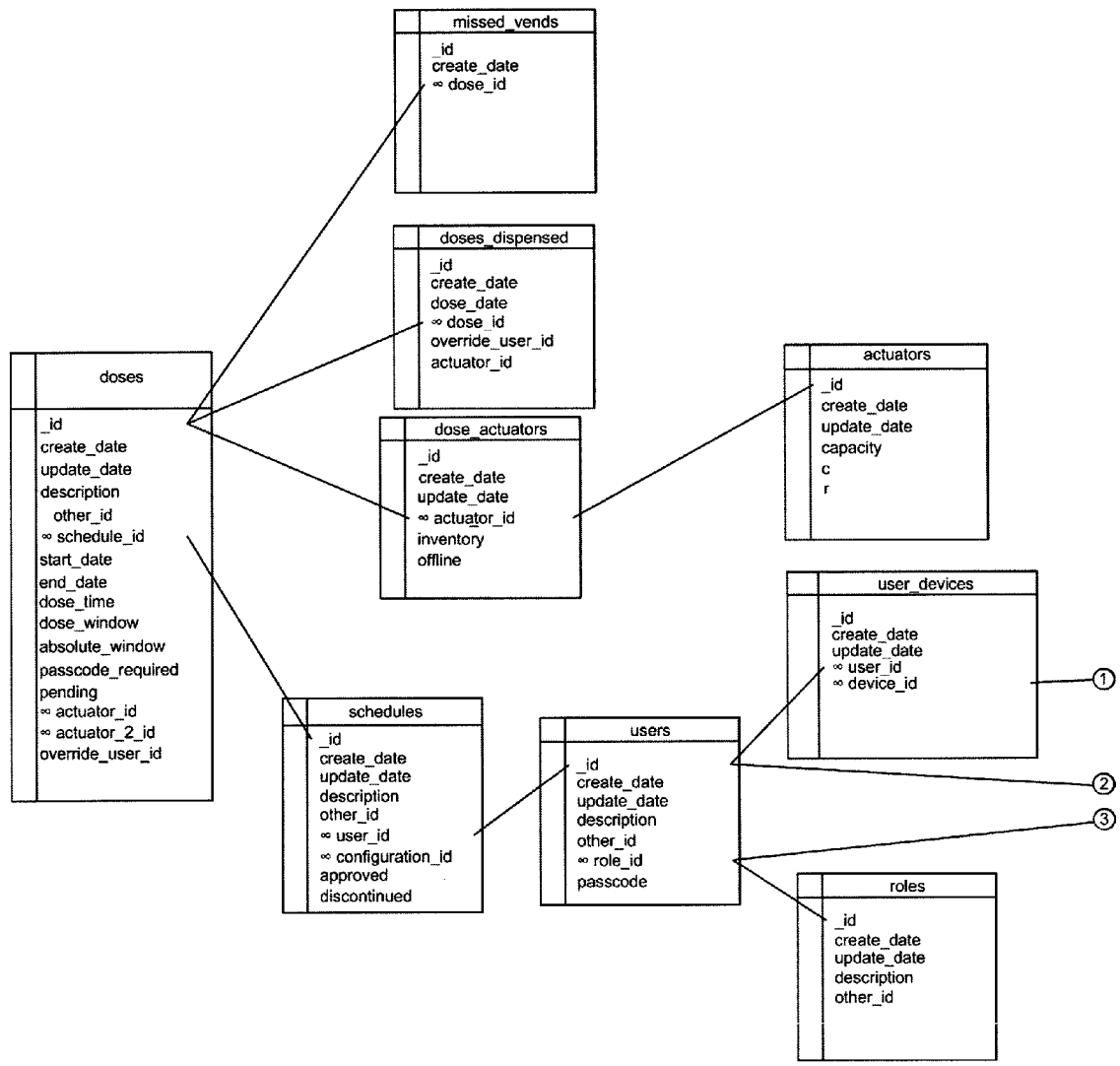
FIGS. 6a-6b and FIG. 7 are Entity Relationship Diagrams (ERDs) for one preferred embodiment of a second implementation.
Figure 6B:
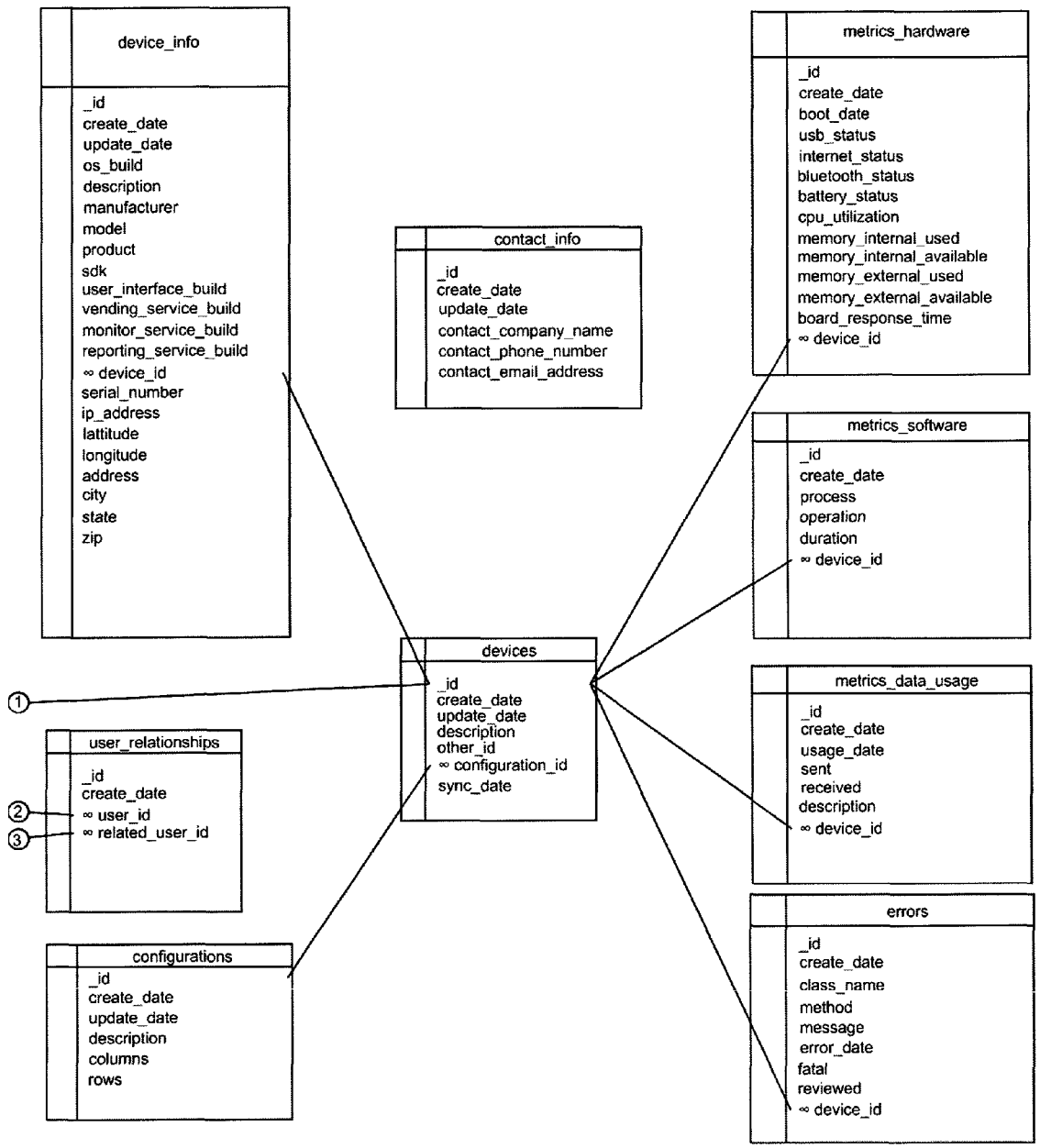
Figure 7:
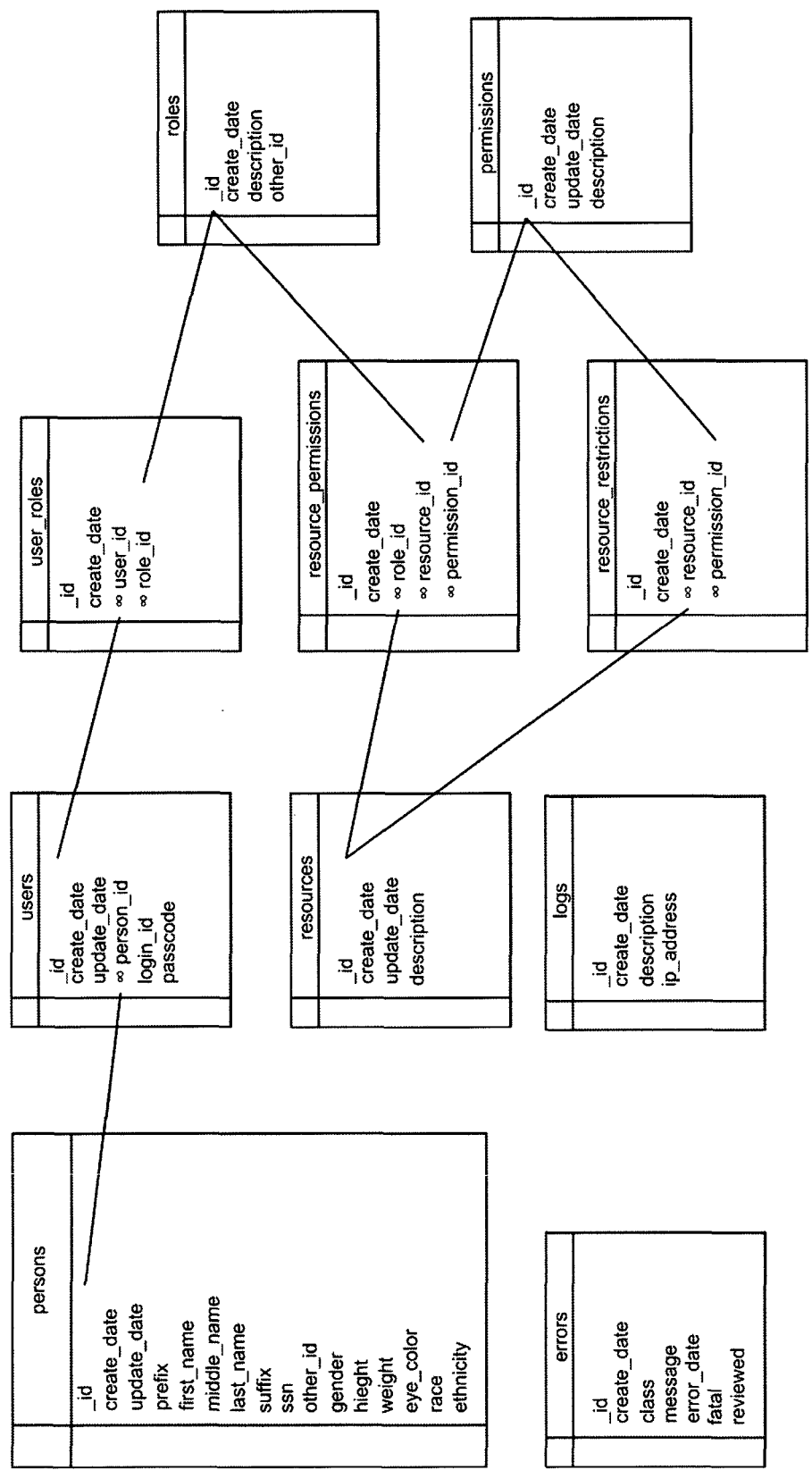

FIGS. 6*a*-6*b* and FIG. 7 are Entity Relationship Diagrams (ERDs) for one preferred embodiment of Implementation 2.

Application—(FIGS. 6*a*-6*b*) The application database is used by the web service to aggregate all device information into a homogenous data set. The structure and entity relationships are identical to that of the database located on each vending machine's Android™ tablet. The web application also uses the application database for displaying data, monitoring, maintenance, and administration.

System (Web Service)—(FIG. 7) The web service and accompanying web application use the System database for basic functions: record web service/application specific errors, authentication and resource access as well as logging and transaction services.

See the Appendix for the database definitions.

Processes

Detailed flow diagram (flowchart) of the steps followed in the process.

Vending Controller—User Interface

Figure 8A:
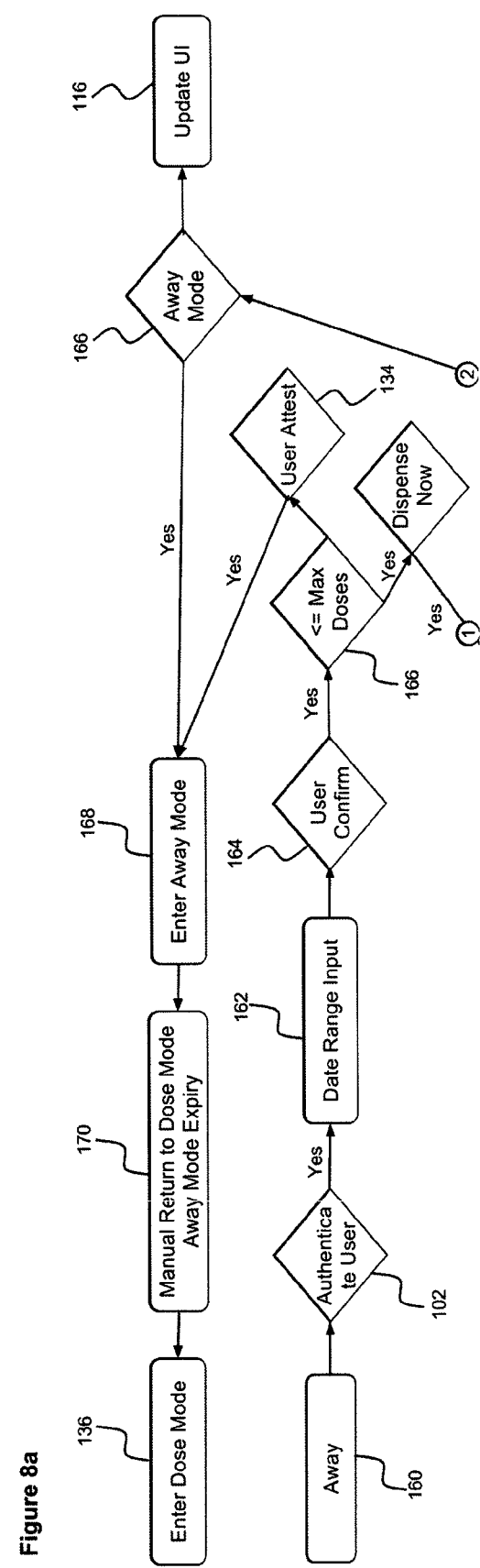
FIGS. 8a-8c, 9, 10a-10e, 11 and 12 show flowcharts of vending machine process controls for use in one preferred embodiment of the second implementation.
Figure 8B:
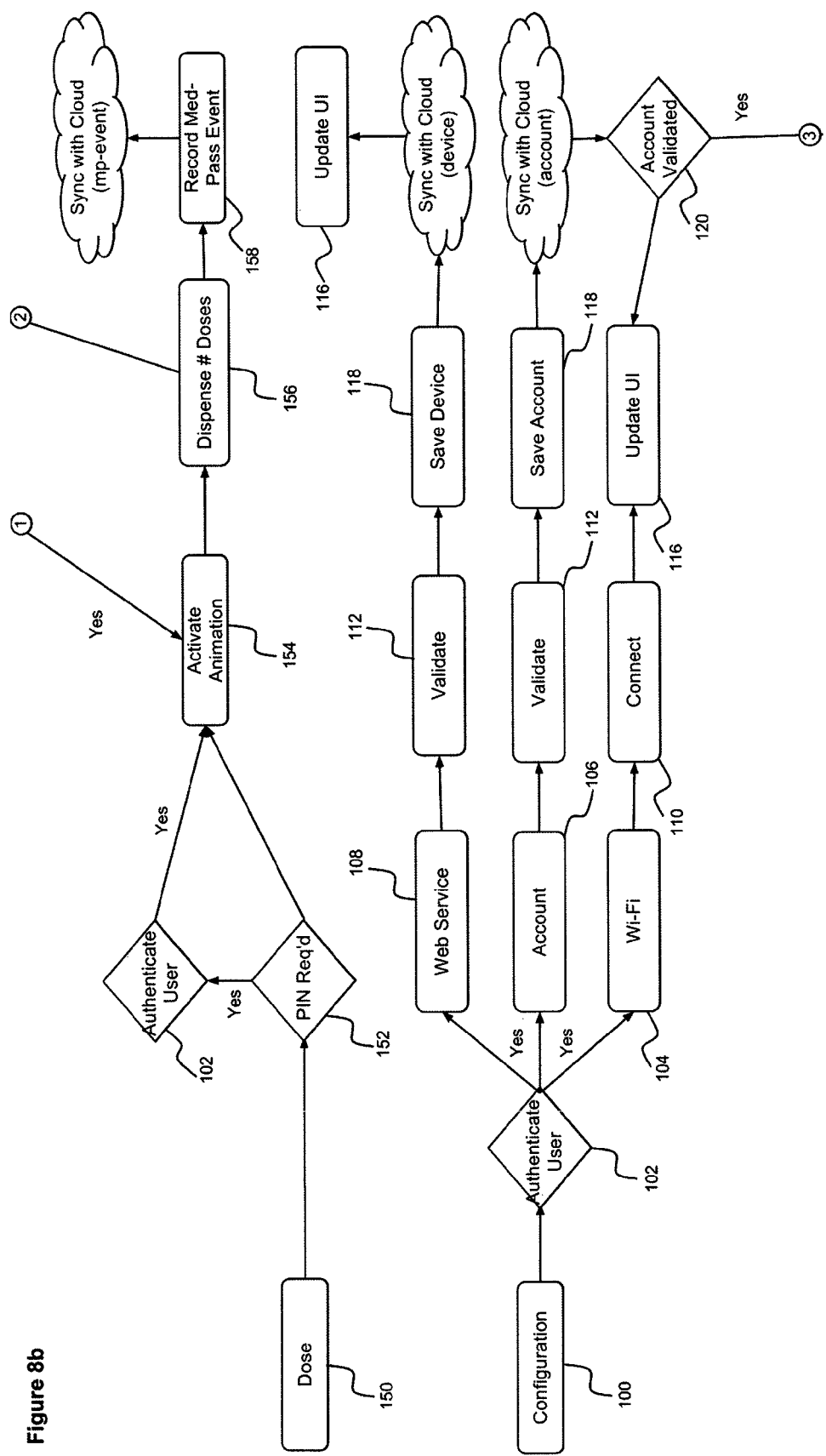
Figure 8C:
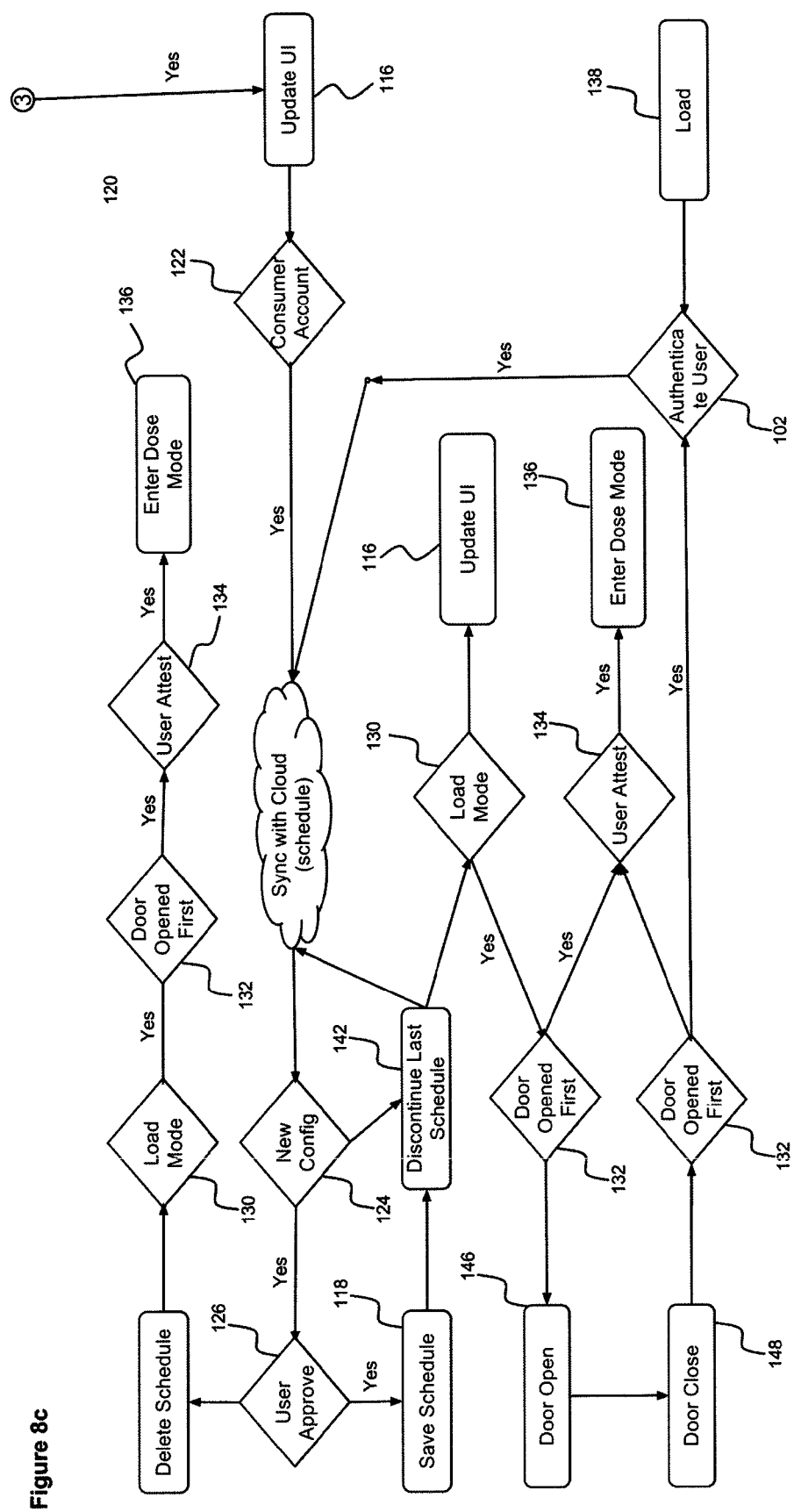

FIGS. 8*a*-8*c*, taken together, show the main vending controller user interface (user-tablet) process flow.

- 100: User taps the configuration button on the main screen to enter Configuration Mode. Configuration Mode provides access to information on the vending machine like: IP address, internet status, CPU usage, available memory, software version information, vending machine health and more. Furthermore, Configuration Mode is where input is made to instruct the vending controller on web service address, authentication credentials, and create and maintain user accounts.
- 102: Authenticate the user as having privileges to perform the requested action or gain access to an area of the user interface that requires certain privileges. This process compares the user's input to that stored with the user configuration section. Since only a PIN is entered, each PIN must be unique within a given vending machine in order to identify the user.
- 104: Configure Wi-Fi connection. Choose from available Wi-Fi access points, set up security and make the connection.
- 106: Configure User (Administrator, Consumer) Accounts. Administrator accounts have full privileges for a given vending machine. Administrators can create other administrators, consumer users and change the web service information. Furthermore, they can gain access to put the vending controller into and take it out of Load Mode.
- 108: Configure web service host address, credentials and device location information. In order for the vending machine to communicate with the web services to push Medpass events, obtain scheduling information and validate administrators and consumers, the address to and credentials for the web service need to be able to be input into the vending controller.
- 110: Connect to Wifi host. Displays current connection status, connection speed and security protocol used.
- 112: Validate user input with respect to the type of information of entered. Before information is pushed to the web service for confirmation or rejection, the data will be validated for reasonableness. Date information must be a date, PIN and it's confirmation field must match and be unique to the vending machine, and all required fields must be populated.
- 116: Refresh the user interface with respect to operational mode. If the vending controller is in Configuration mode, then refresh the display with the information respective of the view: Device information, web service, accounts, Wifi, etc. . . .
- 118: Save data to database. Whether account, connection or Medpass event information, data will be saved to the local Sqlite database.
- 120: If user account was authenticated with the Medpass service, then refresh account listings and proceed, otherwise inform the user that authentication failed.
- 122: If the account type is a consumer account, proceed to request the current dosing schedule for that particular consumer.
- 124: If the schedule is the first schedule used for the consumer, or the configuration of the dosing changes, then prompt the user for approval before continuing.
- 126: The user must approve a new dosing configuration to insure that the medicine packed into the vending machine matches the dosing configuration that the controller uses to vend medication.
- 128: If the user decides not to approve the schedule, it is deleted from the local database and vending continues with the currently approved schedule.
- 130: Dose schedule confirmation can be accessed from two different logical spots in the software. As a result, different paths need to be taken depending upon the controller's operational mode. Determine if the controller is in Load Mode
- 132: There is no physical barrier to prevent a user with the correct keys to gain access to the vending coils inside the vending machine. Proper procedure is to put the vending controller into Load Mode first, then open the open. If this procedure is not followed, then the logical opposite and upon receiving a door open event, the vending controller will remember this action to properly prompt the user for their pin to return the vending machine to Normal Vending Mode.
- 134: Proper loading procedures call for the technician to put the vending machine in load mode before opening the vending machine to load it with medicine. The procedure is designed to ensure the vending machine schedules are synchronized with the MedSupport software, and the medicine packs issued to the technicians for filling the respective vending machines. If the door is opened first, the synchronization process still occurs, but only after the door has been closed.
- 136: Enter Dose Mode. Dose or vend mode is the default mode in the vending controller.
- 138: The Load Mode button is tapped to put the vending controller into Load Mode.
- 142: Discontinue last schedule. Only one schedule can be active at a time. If the user approves a new schedule with a new configuration, or a new schedule with same configuration is automatically approved, then the previously active schedule's attribute 'discontinued' is set to true in the database
- 146: The door opened event is handled and the vending controller is put into Load Mode.
- 148: The door closed event is handled, but the vending controller remains in Load Mode.
- 150: User taps the away mode button to initiate Away Mode configuration.
- 152: Specific doses can be flagged to require an entered PIN to vend it. Determine if PIN is required to vend dose.
- 154: If vending goes forward, a helpful animation demonstrating how to open the pill packet is displayed on screen while the vending occurs. This also serves to the user as confirmation that the dose is currently being vended.

156: Dispense all doses passed to the vending service. Each dose is processed and an instruction sent to the vending controller board which actuates the coil at the address specified.

158: Record each successful coil actuation as a successful Medpass event.

160: User taps the away mode button on the main screen to enter Away Mode configuration.

162: Away mode date range input. Input form to get the input from the user on the date range for the away mode period. Prompt user for the date range that Away Mode will cover. Date range will cover discrete days, with the accepted start time of 7:00 AM and ending time on 11:00 PM of the end date. All undispensed doses falling partially or entirely within the specified range will be considered the 'target doses' when determining dose count against the Max Dose limit and all dispensed doses in that range will not be counted or targeted.

164: Away mode date range confirm. To double check the users date range input, the user is asked to confirm that what is displayed to them is what they think they entered. If not, the user is provided the ability to alter the dates, and once again confirm input.

166: There is a physical limit to the number of doses the machine can vend at a given time. This limit is commonly known as the 'Max Doses'—The number of doses that can be dispensed at one time without clogging the chute. If the away mode date range dose count falls at or under this amount, then the process continues and Medpass events will occur when the doses are vended. If the amount is above the limit, then the doses required for the away period are to be manually retrieved from the vending machine or the pharmacy and the vending controller will not record Medpass events.

167: This decision is reached if the Max Dose limit is not exceeded. The user is prompted with the choice of dispensing all med packets now, or dispensing at the time the away mode is to start. This prompt is shown only if Away Mode is in the future. If the start of Away Mode is in the past of immediate, then the doses are dispensed without prompting the user. In either case, a Medpass event is recorded for each dose vended.

170: Away Mode Expiry, or manual override of away mode. When the Away Mode reaches the end of it's period, or a manual override command is issued, the vending controller will go back into Dose Mode.

Vending Controller—UI Background Operations

Figure 9:
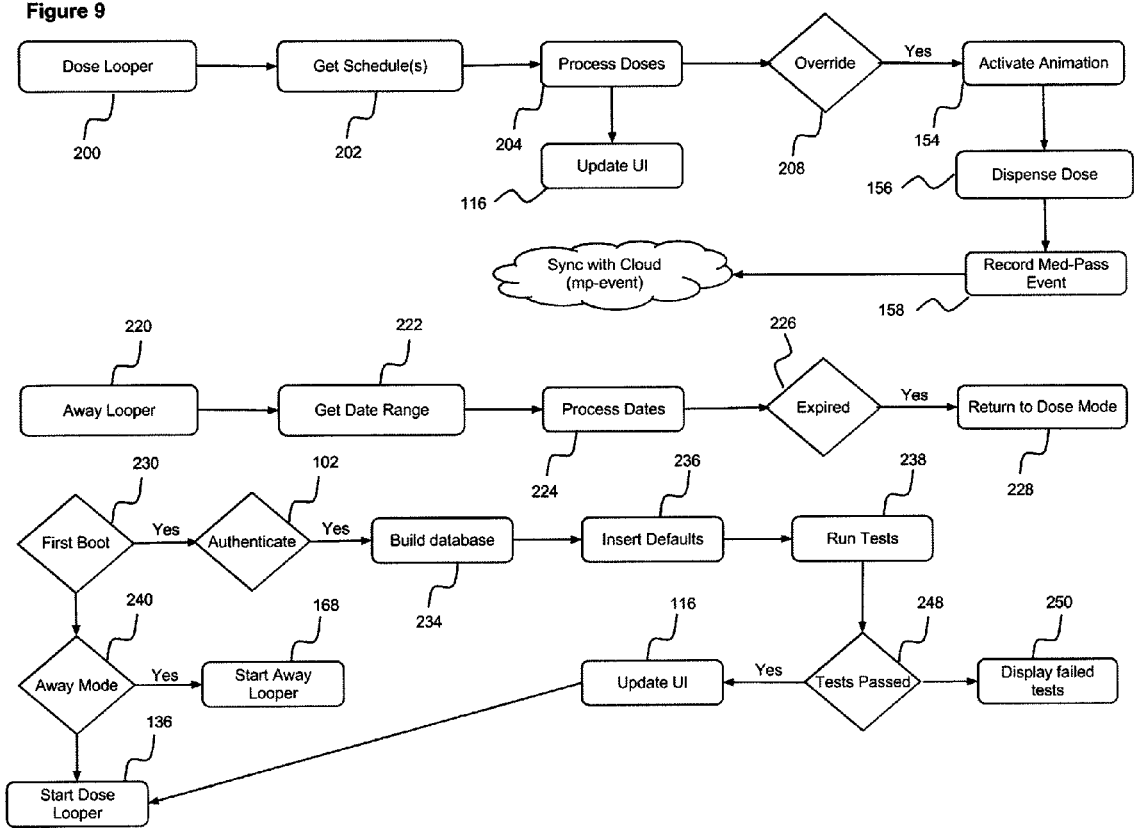
Figure 10A:
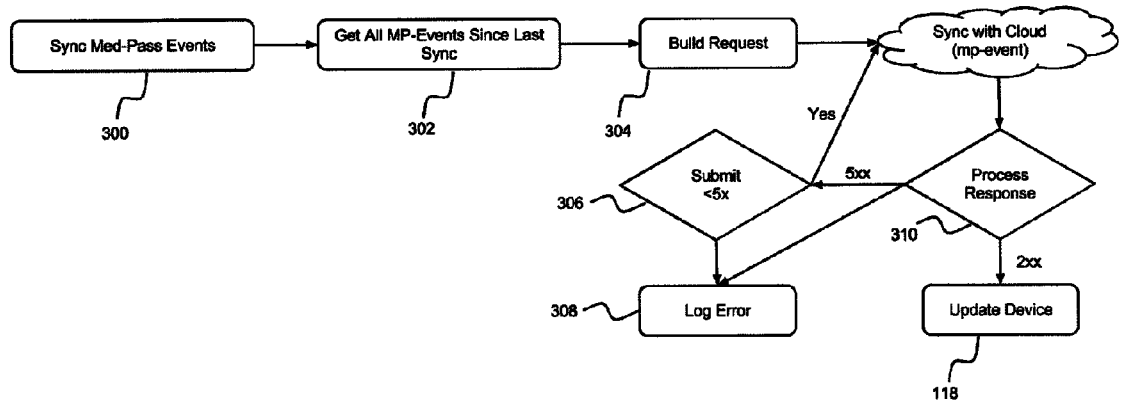
Figure 10B:
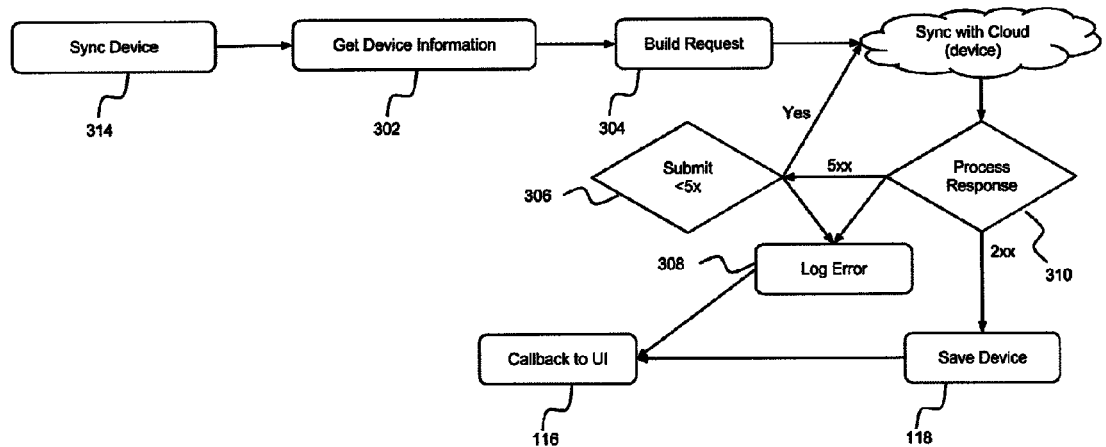
Figure 10C:
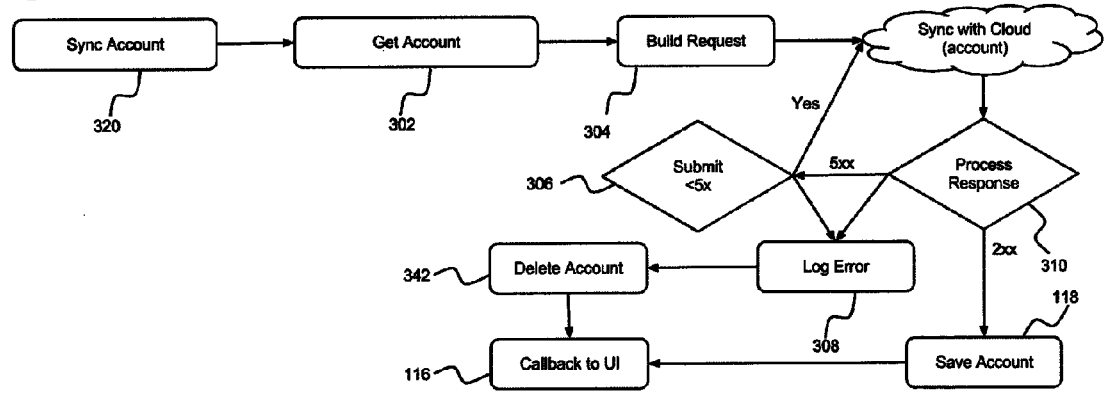
Figure 10D:
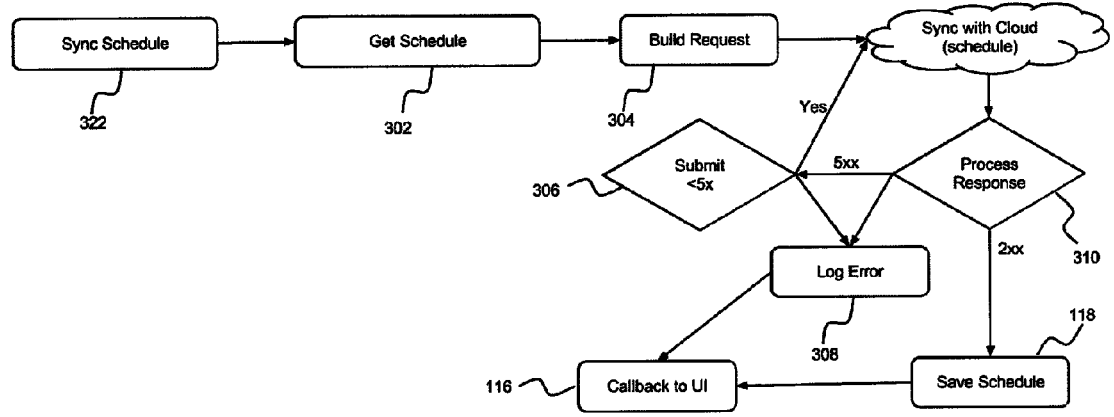
Figure 10E:
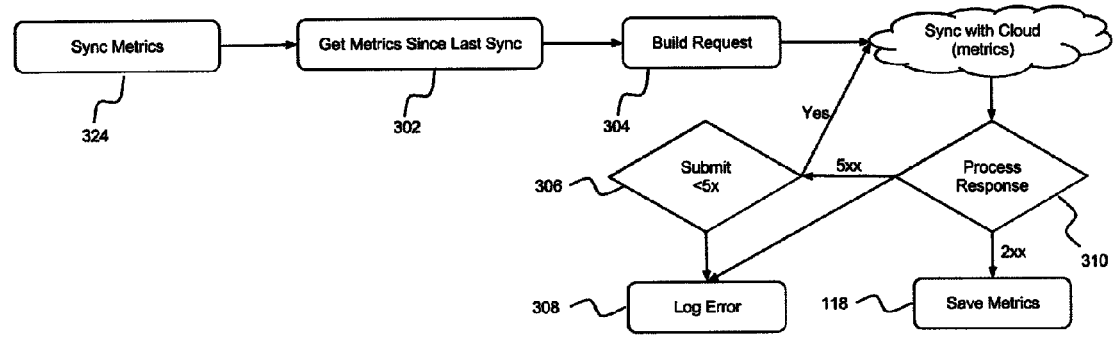

FIG. 9 represents the main vending controller user interface background processes flow.

200: Dose looper starts on entry into Dose Mode (a.k.a. Vend Mode). This is a timed loop firing at the top of every minute whilst in Dose Mode.

202: Retrieve all active schedules from the database.

204: Process doses by examining their dose time compared to current time and their dose status (expired, vended, pending, or queued).

208: If an override order has been directed on a dose, then vend that dose at this time.

220: Away looper starts on entry into Away Mode. This is a timed loop firing at the top of every minute whilst in Away Mode.

222: Get the Away Mode date range.

224: Determine if the Away Mode has expired.

226: If Away Mode has not expired, sleep to the top of the minute.

228: When the Away Mode expires, or a manual override command is issued, the vending controller will go back into Dose Mode.

230: When the tablet is booted into the vending controller for the first time, the system will initialize.

234: On initialization, the system will create the database, and the table structure.

236: The system will then populate the database with certain default data, and build various other constructs to provide vending services.

238: Tests will be automatically executed to insure that the database was built properly and is functioning normally.

240: If the system table is booted and it's not the first boot, then the system will check to see if the current time falls within an Away Mode period.

248: If initialization systems pass tests, then move on.

250: Initialization tests failed. Prompt user.

Vending Controller—Reporting Service

FIGS. 10*a*-10*e*, taken together, represents the vending controller reporting service processes flow.

300: Synchronize Medpass events initiated.

302: Get all data that have not been synchronized with the web service respective of the process.

304: Build the HTTP REST request appropriate to the data being sent.

306: Re-submit any request that fails due to a server error (500 type response), up to 5 times.

308: Log any errors encountered during the synchronization process.

310: Process the web service response to determine success or failure on server.

320: Initiate synchronization of user account.

322: Initiate synchronization of consumer schedule.

324: Initiate synchronization of device performance metrics.

Vending Controller—Monitor Service

FIG. 11 represents the vending controller monitor service processes flow.

400: Initiate the monitor service looper. The monitor service, like the vending controller user interface, always runs when the tablet is powered on, but in the background.

402: Retrieve hardware metrics by polling the vending controller board and the tablet hardware.

404: Retrieve the software metrics from the database. Software metrics are collected when each process runs.

406: Retrieve the statistics on the amount of data that has been transmitted for the current day.

408: Determine if it Is it time to aggregate the metrics.

410: Once a day, the all the measurements taken will be aggregated to reduce the amount of data that will be sent to the server. Aggregation will take the mean average of the data populate by metric.

412: Save the individual or aggregated metrics to the database.

414: Determine if the vending controller is registered with the web service.

416: Determine the operational status of the other apps. If they are not currently running and should be, then start each respectively as necessary.

Vending Controller—Vending Service

Figure 12:
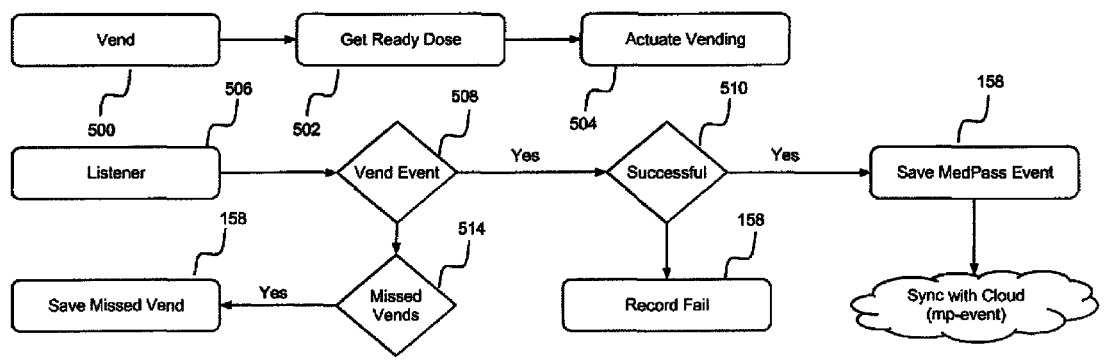

FIG. 12 represents the vending controller vending service processes flow.

500: Initiate the vending service.

502: Extract the dose to be dispensed from the request.

504: Send instruction to the vending controller board to actuate the motor at the specified address.
506: Listen for events raised from the board on a port.
508: Determine if the event raised is a vending event.
510: Determine if the vending event successful.
514: Determine if the event raised is a missed vend event.

Web Service (Cloud)—API Resources

Figure 13:
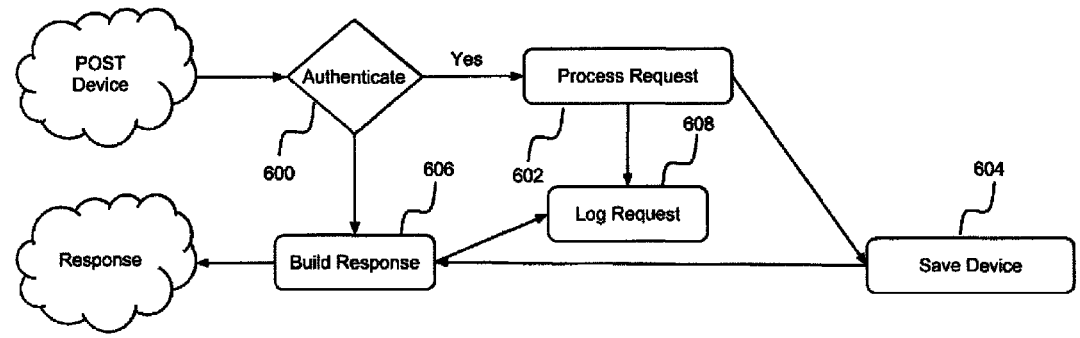
FIGS. 13-19 show flowcharts of Medherent web service processes for use in one preferred embodiment of the second implementation.

FIG. 13—represents the Medherent web service PMVD registration processes flow.

Figure 14:
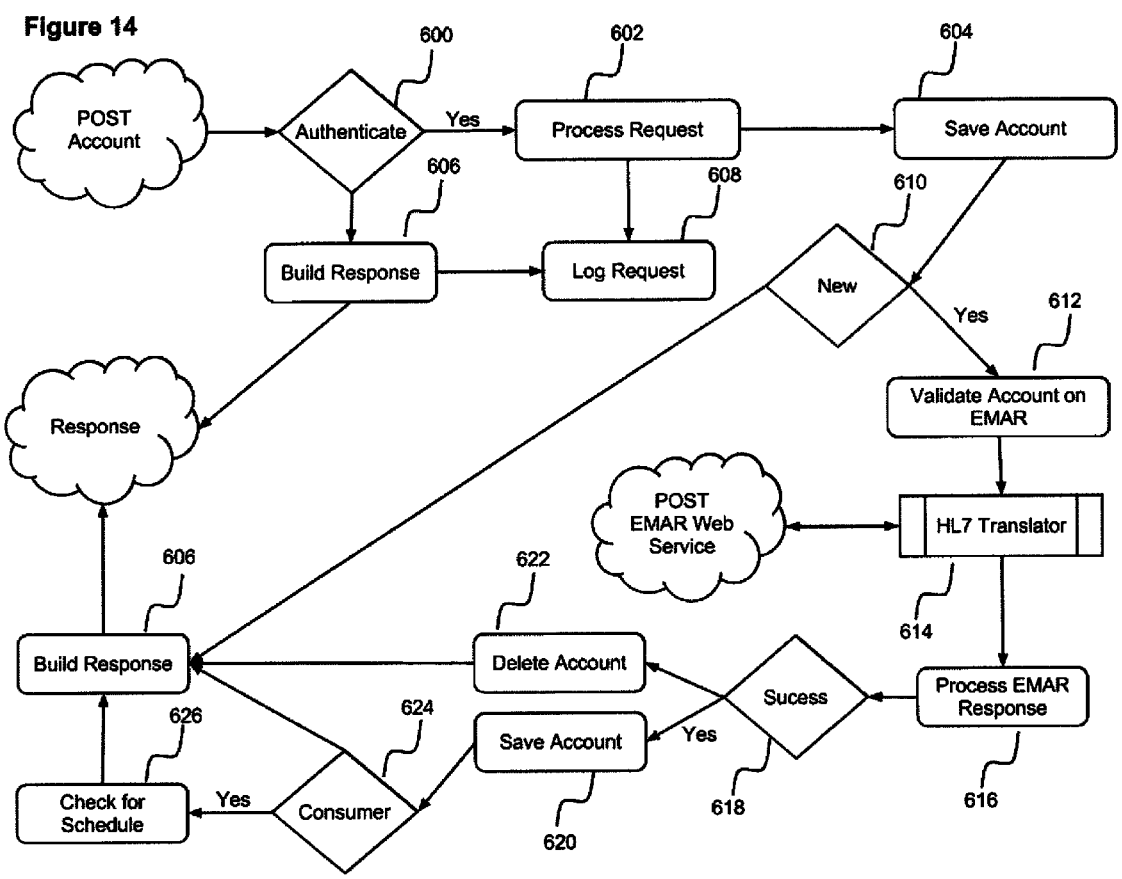

FIG. 14—represents the Medherent web service user/consumer registration processes flow.

Figure 15:
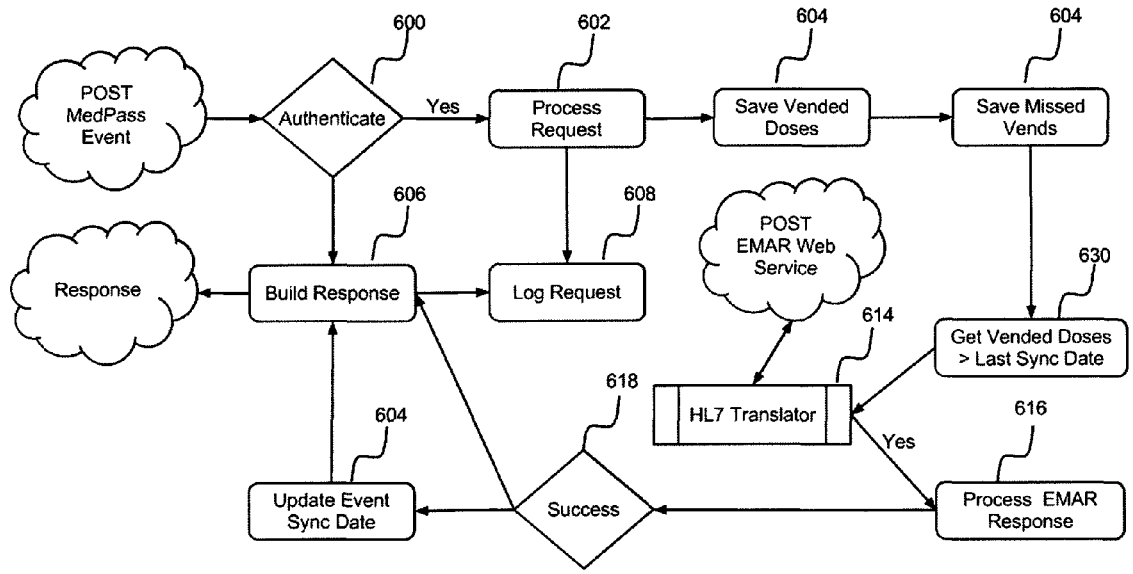

FIG. 15—represents the Medherent web service medpass event processes flow.

Figure 16:
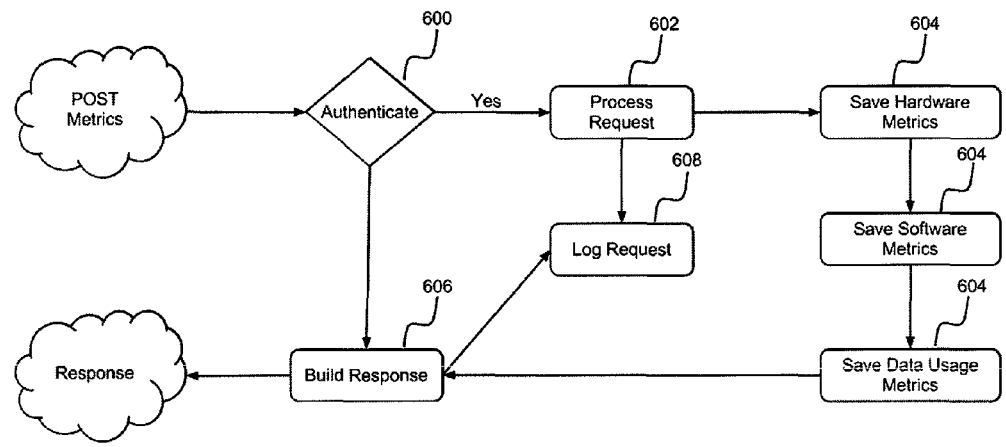

FIG. 16—represents the Medherent web service PMVD metrics upload processes flow.

Figure 17:
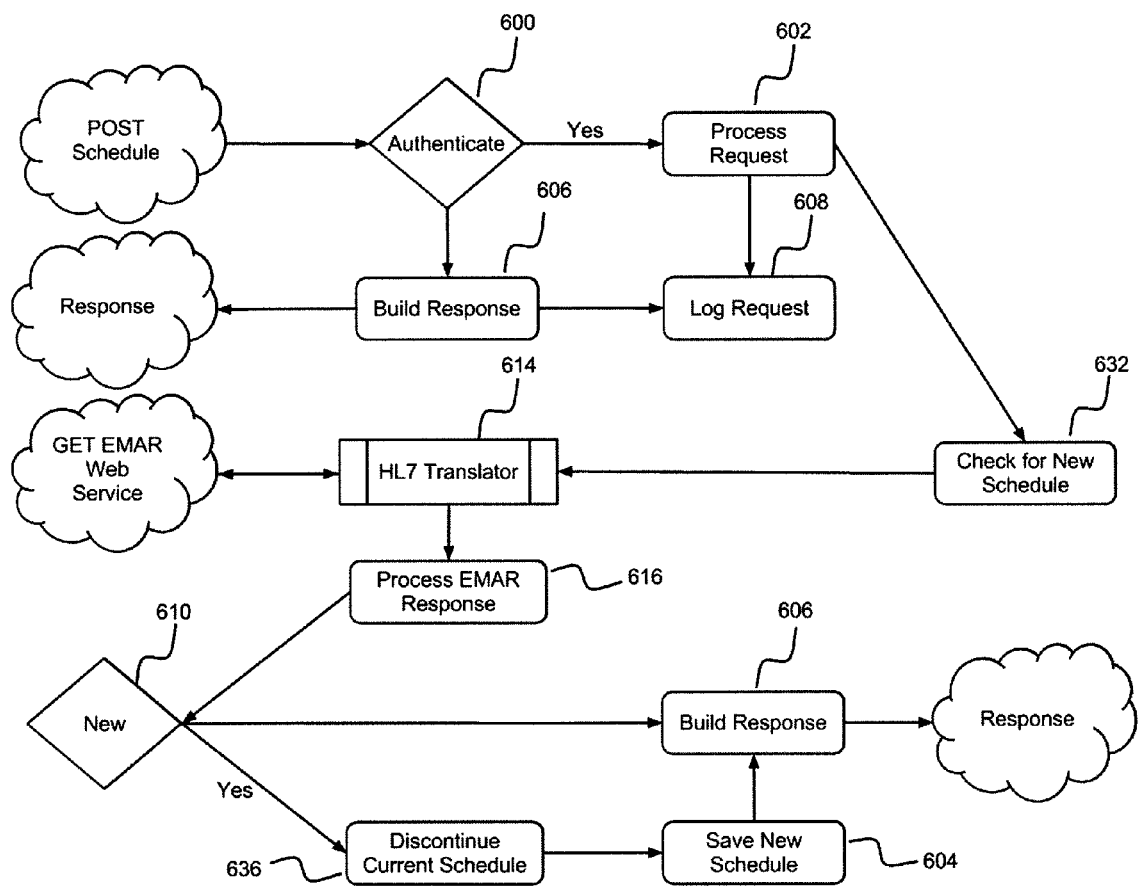

FIG. 17—represents the Medherent web service validate/update schedule processes flow.

Figure 18:
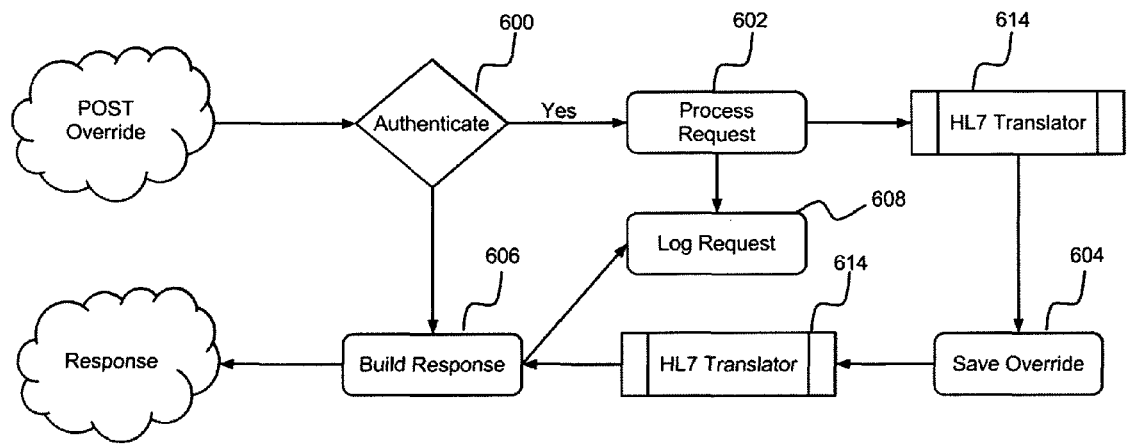

FIG. 18—represents the Medherent web service dose override process flow.

Figure 19:
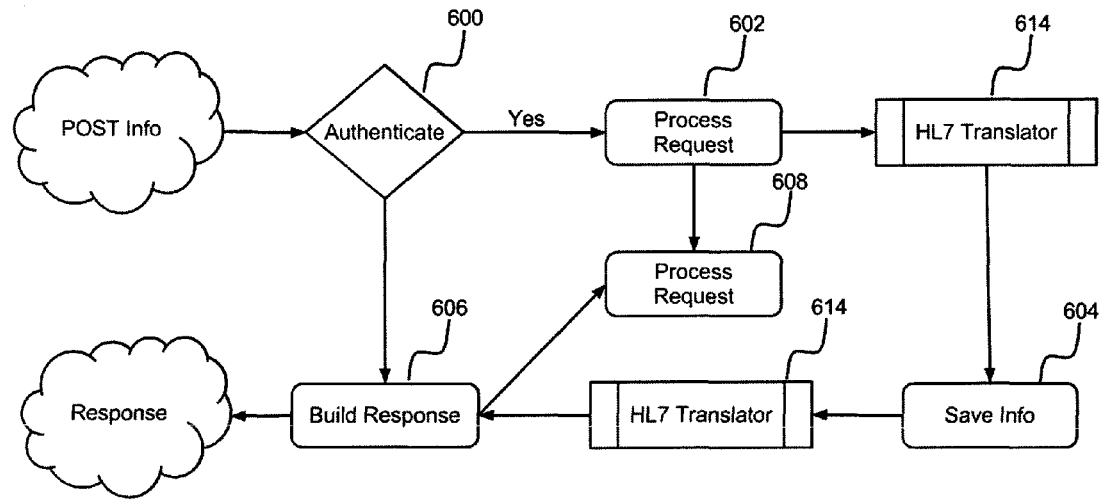

FIG. 19—represents the Medherent web service contact info exchange process flow.

600: Authenticate the post.
602: Process the incoming post information and parse out the device entity.
604: Update the network database
606: Build and send response back to the client to inform of success or failure.
608: Log the request and request information
610: Determine if the post is for a new or existing record.
612: The account is new so validate the it against Medsupport.
614: Translate the request to Medsupport into an HL7 transaction. Translate the response from Medsupport out of the HL7 transaction.
616: Process Medsupport response
618: Determine if Medsupport authenticated the account.
620: Update the network database with Medsupport AccountId.
622: Delete the account from the network database.
624: Determine if the account is a consumer account.
626: Check for consumer's schedule. See FIG. 12 for details.
630: Get all medpass events that have not been synchronized with Medsupport.
632: Check for a new schedule in Medsupport
636: Mark the current schedule for the respective consumer as discontinued.

HL7 Translator

In order for Medherent to perform its duties and dispense dose packets at the correct times to the correct consumer, Medherent must pass certain data to the MedPass system for identification, and receive data back in the form of a schedule or validation.

Assumptions:

There are two types of User, both of which must exist in MedSupport before registration.
 1. Administrator
 2. Consumer Web Services will expect an HTTP REST call
 1. Headers
    a. User
    b. Pass
 2. Body containing an HL7 formatted message.

Transactions

Administrator registration
Consumer registration
Override dispense
Medpass event
Contact information Header Used in all Requests to Medsupport
 Medherent
 Machine number
 Company code
 DateTime of transaction
 Transaction number Request
 MSH|^~\&|Medherent|{MachineNumber}|CARASOLVA|{CompanyCode}|{DateTime yyyyMMddhhmmss}||ADT^A01|{transaction number}||2.3|1|

Header Used in all Requests to Medherent
 Carasolva
 Medherent
 Company code
 DateTime of transaction
 Transaction number Request
 MSH|^~\&|Carasolva|CMS|Medherent|CompanyCode|DateTimeTransactionSent||RDS^O13|TransactionNumberFromRegisterTransaction|P|2.5|||||ASCII|

Administrator Registration
 Key Data:

| PV1.2.3 | Company code |
| PV1.2.0 | Location code |
| PID.2.0 | Medsupport LoginId |
| PID.2.1 | Initials |

Request Message to MedSupport
 MSH|^~\&|Medherent|{MachineNumber}|CARASOLVA|{CompanyCode}|{DateTime yyyyMMddhhmmss}||ADT^A01|{transaction number}||2.3|1|
 PID|1|{MedSupportLogirad}|{UserInitials}|||||
 PV1|1||{LocationCode}^^^{CompanyCode}|

MedSupport Acknowledgement Message
 MSH|^~\&|Carasolva|{MachineNumber}|Medherent|{CompanyCode}|{DateTime yyyyMMddhhmmss}||ADT^O11|{transaction number}|ACK|2.3|1|
 MSA|{Response Code}|{Response text}|
 ERR|Error Code and Location|Error Location|HL7 Error Code||Severity|||||

Response Codes:
 AA—Accepted
 AE—Application Error
 ER1—Medsupport User Name not found
 ER2—Medsupport User Name found, but inactive
 ER3—Medsupport User Name found but access to location denied Key Data:

| PID.3 | Medsupport UserId |

MedSupport Response Message
 MSH|^~\&|Carasolva|CMS|Medherent|CompanyCode|DateTimeTransactionSent||RDE^O01|TransactionNumberFromRegisterTransaction|P|2.5|||||ASCII
 PID|1||MedsupportUserId|LastName||DateOfBirth||||||||||SSN4digits|
 PV1|1|| LocationCode^^^CompanyCodeGoe|

Medherent Acknowledgement Message
MSH|^~\&|Medherent|MH|Carasolva|CompanyCode GoesHere|DateTimeTransactionSent||RDE^O13|TransactionNumber|P|2.5|||||ASCII|||
    MSA|Message Control ID|TransactionNumberFromRegisterTransaction|

Response Codes:
    AA—Accepted
    AE—Application Error
    ER1—Error Description Consumer Registration
    Key Data:

| | |
|---|---|
| PV1.3.0 | Company code |
| PV1.3.3 | Location code |
| PID.22 | Last 4 digits of SSN |
| PID.5 | Last name |
| PID.6 | Date of Birth |

Request Message to MedSupport
MSH|^~\&|Medherent|{MachineNumber}|CARASOLVA|{CompanyCode}|{DateTime yyyyMMddhhmmss}||ADT^A01|{transaction number}||2.3|1|
    PID|1||||LastName|DOB|||||||||||SSN|
    PV1|1|||{LocationCode}^^^{CompanyCode}|

MedSupport Acknowledgement Message
MSH|^~\&|Carasolva|{MachineNumber}|Medherent|{CompanyCode}|{DateTime yyyyMMddhhmmss}||ADT^O11|{transaction number}|ACK|2.3|1|
    MSA|{Response Code}|{Response text}|
    ERR|Error Code and Location|Error Location|HL7 Error Code||Severity|||||

Response Codes:
    AA—Accepted
    AE—Application Error
    ER1—Medsupport Consumer not found
    ER2—Medsupport Consumer found, but inactive
    Key Data:

| | |
|---|---|
| TQ1.4 | Schedule |
| PID.3 | Medsupport ConsumerId |

MedSupport Response Message
MSH|^~\&|Carasolva|CMS|Medherent|CompanyCode|DateTimeTransactionSent||RDE^O01|TransactionNumberFromRegisterTransaction|P|2.5|||||ASCII
    PID|1||MedsupportConsumerId|LastName||DateOfBirth|||||||||SSN4digits|
    PV1|1|1I LocationCode^^^CompanyCodeGoe|
    TQ1|1|||0800,1200,2000|

Medherent Acknowledgement Message
MSH|^~\&|Medherent|MH|Carasolva|CompanyCode GoesHere|DateTimeTransactionSent||RDE^O13|TransactionNumber|P|2.5|||||ASCII|||
    MSA|Message Control ID|TransactionNumberFromRegisterTransaction|

Response Codes:
    AA—Accepted
    AE—Application Error
    ER1—Error Description Override Dispense
    Key Data:

| | |
|---|---|
| PID.3 | Medsupport ConsumerId |
| TQ1.4 | Dose time |

Request Message to Medherent
MSH|^~\&|Carasolva|CMS|Medherent|CompanyCode|DateTimeTransactionSent||RDS^O13|TransactionNumberFromRegisterTransaction|P|2.5|||||ASCII|
    PID|1||MedsupportConsumerId|||||||||||
    TQ1|1|O||0800|

Medherent Acknowledgement Message
MSH|^~\&|Medherent|MH|Carasolva|CompanyCode GoesHere|DateTimeTransactionSent||RDE^O13|TransactionNumber|P|2.5|||||ASCII|||
    MSA|Message Control ID|TransactionNumberFromRegisterTransaction|
    ERR|Error Code and Location|Error Location|HL7 Error Code||Severity|||||

Response Codes:
    AA—Accepted
    AE—Application Error
    ER1—Error Description Medpass Event
    Key Data:

| | |
|---|---|
| PID.3 | Medsupport ConsumerId |
| RXD.3 | MedPass Date Time |
| RXD.4 | Medherent ConsumerId |

Request Message to MedSupport
MSH|^~\&|Medherent|MH|Carasolva|CompanyCode|DateTimeTransactionSent||RDS^O13|TransactionNumber|P|2.5|||||ASCII|||
    PID|1||MedSupportConsumerId|||||||||||
    RXD|1||Medpass datetime|MedherentConsumerId|

MedSupport Acknowledgement Message
MSH|^~\&|Carasolva|{MachineNumber}|Medherent|{CompanyCode}|{DateTime yyyyMMddhhmmss}||ADT^O11|{transaction number}|ACK|2.3|1|
    MSA|{Response Code}|{Response text}|
    ERR|Error Code and Location|Error Location|HL7 Error Code||Severity|||||

Response Codes:
    AA—Accepted
    AE—Application Error
    ER1—Error Description Contact Information
    Key Data:

| | |
|---|---|
| EVN.6.0 | Company Name |
| EVN.6.1 | Phone number |
| EVN.6.2 | Email address |

Request Message to Medherent
MSH|^~\&|Carasolva|CMS|Medherent|CompanyCode|DateTimeTransactionSent||ADT^O08^ADT^O03|TransactionNumber|P|2.5|||||ASCII|||
    EVN|20100512162022|||||CompanyName^Phone Number^EmailAddress|

Medherent Acknowledgement Message

MSH|^~\&|Medherent|MH|Carasolva|CompanyCode GoesHere|DateTimeTransactionSent||RDE^O13|TransactionNumber|P|2.5|||||ASCII|||

MSA|Message Control ID|TransactionNumberFromRegisterTransaction|

ERR|Error Code and Location|Error Location|HL7 Error Code||Severity|||||||

Response Codes:
- AA—Accepted
- AE—Application Error
- ER1—Error Description

Request Message to MedSupport

MSH|^~\&|Medherent|MH|Carasolva|CompanyCode|DateTimeTransactionSent||ADT^O08^ADT^O03|TransactionNumber|P|2.5|||||ASCII|||

EVN|20100512162022|||||CompanyName^Phone Number^EmailAddress

MedSupport Acknowledgement Message

MSH|^~\&|Carasolva|{MachineNumber}|Medherent|{CompanyCode}|{DateTime yyyyMMddhhmmss}||ADT^O11|transaction number-|ACK|2.3|1|

MSA|{Response Code}|{Response text}|

ERR|Error Code and Location|Error Location|HL7 Error Code||Severity|||||||

Response Codes:
- AA—Accepted
- AE—Application Error
- ER1—Error Description

Since the dosing schedule is not specifically designed to accommodate a vending machine's language and data structure, it needs to be mapped to the physical hardware (Paired) so that the pharmacy and pharmacy tech filling the machine get the correct medications vended at the correct time and records reflect the physical arrangement. Furthermore, the vending controller needs to know which motor to actuate when a dose needs vending. To accomplish that, a map that translates the doses into a motor map is used. This map can be one of six configurations and is described in the following list:

Configurations Supported
- a. 1 time per day
  - i. Dose 1 (Tray 1: Selection: 1 & 2)
- b. 2 times per day
  - i. Dose 1 (Tray 1: Selection: 1 & 2)
  - ii. Dose 2 (Tray 2: Selection: 1 & 2)
- c. 3 times per day
  - i. Dose 1 (Tray 1: Selection: 1 & 2)
  - ii. Dose 2 (Tray 2: Selection: 1 & 2)
  - iii. Dose 3 (Tray 3: Selection: 1 & 2)
- d. 4 times per day
  - i. Dose 1 (Tray 1: Selection: 1)
  - ii. Dose 2 (Tray 1: Selection: 2)
  - iii. Dose 3 (Tray 2: Selection: 1)
  - iv. Dose 4 (Tray 2: Selection: 2)
- e. 5 times per day
  - i. Dose 1 (Tray 1: Selection: 1)
  - ii. Dose 2 (Tray 1: Selection: 2)
  - iii. Dose 3 (Tray 2: Selection: 1)
  - iv. Dose 4 (Tray 2: Selection: 2)
  - v. Dose 5 (Tray 3: Selection: 1)
- f. 6 times per day
  - i. Dose 1 (Tray 1: Selection: 1)
  - ii. Dose 2 (Tray 1: Selection: 2)
  - iii. Dose 3 (Tray 2: Selection: 1)
  - iv. Dose 4 (Tray 2: Selection: 2)
  - v. Dose 5 (Tray 3: Selection: 1)
  - vi. Dose 6 (Tray 3: Selection: 2)

Figure 40:
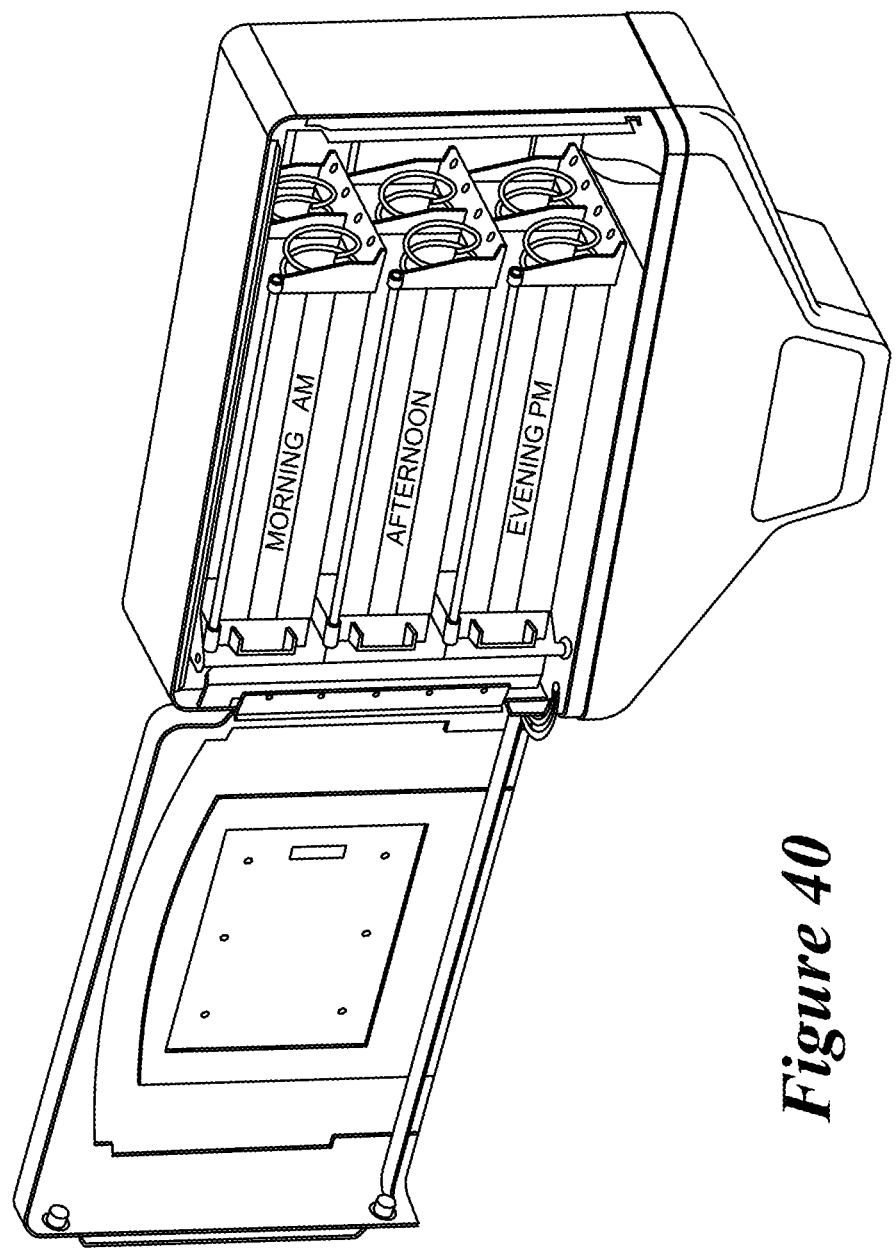
FIG. 40-42 show different views of a PMVD that is suitable for use in the second implementation.

Referring to FIG. 40 which shows a vending machine which is suitable for up to a "3 times per day" configuration and which has its front panel door open, Tray 1 is the topmost pair of helical coils labeled "MORNING AM", Tray 2 is the middle pair of helical coils labeled "AFTERNOON" and Tray 3 is the bottommost pair of helical coils labeled "EVENING PM." Selection 1 and Selection 2 refer to respective ones of the pair of helical coils.

Using the row/column explanation discussed below with respect to step 1104, the row represents the tray and the column in the row represents the Selection 1 or 2, such that in the vending machine of FIG. 40, there is a matrix of three rows and two columns when viewed in GVC terminology?

IMPLEMENTATION 1 refers to a vending slot or column that medications are vended from. Each vending slot or column in IMPLEMENTATION 1 is equivalent to a Tray #/Selection # or a row/column of a matrix in IMPLEMENTATION 2.

Figure 42:
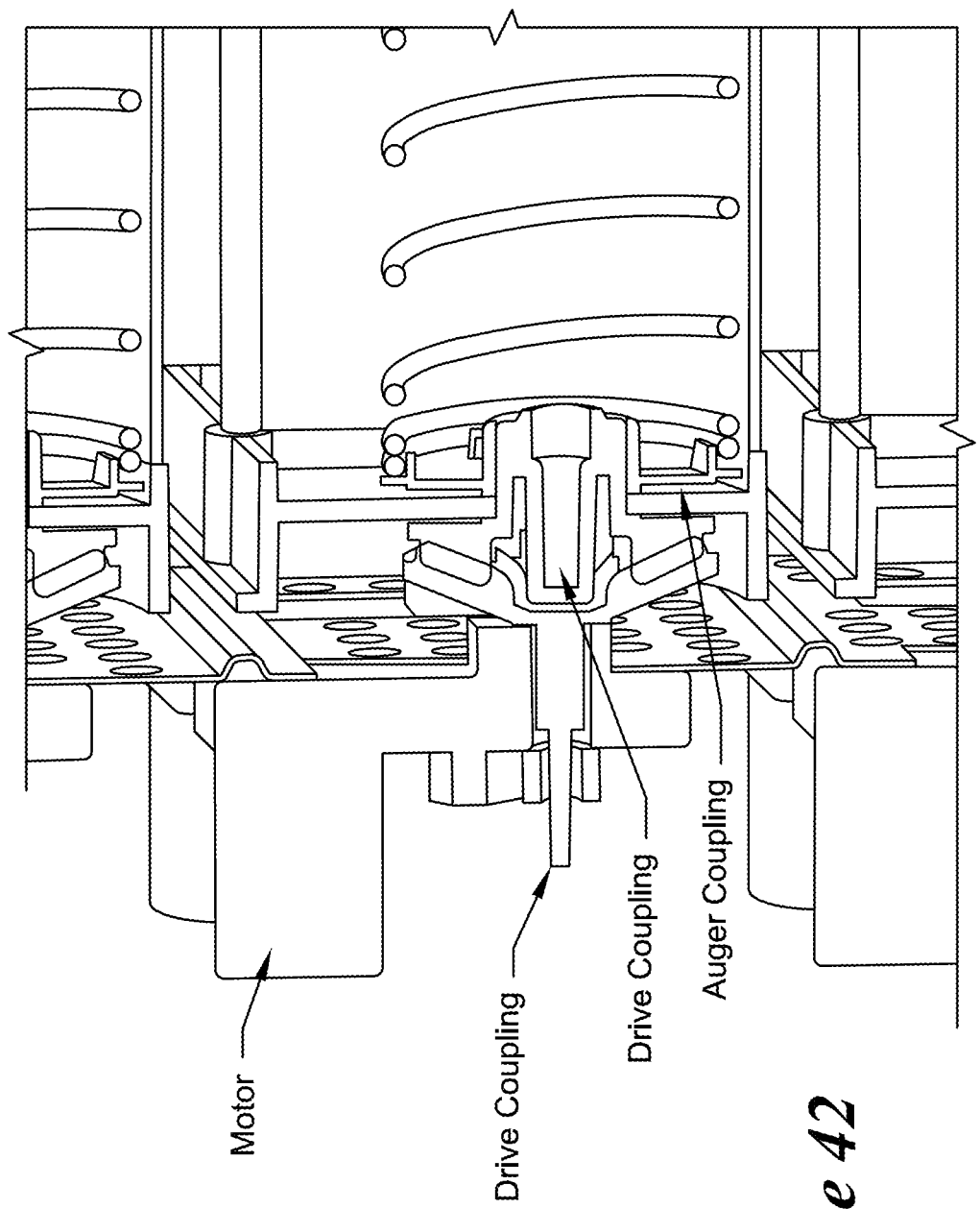

FIG. 42 shows an example of motor and drive elements for the respective helical coils. There is a separate motor for each helical coil.

The dosing algorithm is fairly straightforward. Doses have a dose time and a date. When the current time and date falls within the dosing window, as defined by the dose date and time plus a vending window beyond the dose time (currently 2 hours), then the dose is considered pending. When a dose is pending, the "Dispense My Meds" button is displayed along with a multi-tonal audio sound. If no dose is in a pending state, then the doses are listed with their current status (dispensed, queued or --). Where "--" signifies that the dosing window has closed and the dose was not dispensed.

If the consumer taps the "Dispense My Meds" button, the vending of the medication packet begins. The dose motor pairing in the vending machine is determined with the intermediate web services when the schedule POST is sent from the eMAR web service. When it's time to vend a particular dose, the vending service algorithm retrieves the dose actuator(s) paired with the particular dose and reviews the current inventory level for 1) to ensure that there is an inventory item to vend and is online, and 2), if there is more than one actuator paired, that it vends from the particular actuator that has the largest inventory level greater than zero and is online. This provides 2 benefits, 1) that upon the failure of a motor in a multiple pairing situation, that the other can act as a failover until the vending machine can be serviced and repaired. Once the particular actuator address is resolved, the vending instruction is then communicated to the Global Vending Controller (GVC) board over serial communication using a USB cable. This instruction in general is !SEL_LF where SEL represents the 3 digit selection number pertaining to the actuator address that is recognized by the GVC board.

Schedule Translation Mapping

Translating the HL7 formatted schedule information begins with parsing the message segments to extract the data and determine the consumer, and their respective schedule. The schedule information is contained in a tuple field with dose times delimited by commas.

The HL7 transaction amounts to a RESTful web service POST where the body entity contains the HL7 formatted message:

MSH|^~\&|Carasolva|CMS|Medherent|CompanyCode|DateTimeTransactionSent||RDE^O01|TransactionNumberFromRegisterTransaction|P|2.5|||||ASCII PID|1||MedsupportConsumerId|LastName||DateOf
Birth|||||||||SSN4digits|
PV1|1|LocationCode^^^CompanyCode|
TQ1|1|||0800,1200,2000|

The message segments of particular interest are the PID segment field 3, and the TQ1 segment field 4. Field 4 of the TQ1 segment as stated earlier is a tuple field, so the data must be split into its component parts resulting in an array of dose times. The dose times are then counted, omitting any empty tuple items. There are 6 pre-determined configurations that map the dose times into actuator relationships. So, determining which configuration to use is a matter of determining the number of doses per day then applying the configuration map.

Once the map is created, the data is saved in the database for retrieval. If a schedule already exists for the consumer, the existing schedule is marked discontinued and the new schedule takes over.

User Interface Images—Vending Controller

FIGS. 20-32 represent the various user interface screens that initiate and prompt the user as well as provide a vehicle for entering information into the system. Furthermore, it allows the user to put the vending controller into certain modes.

Figure 20:
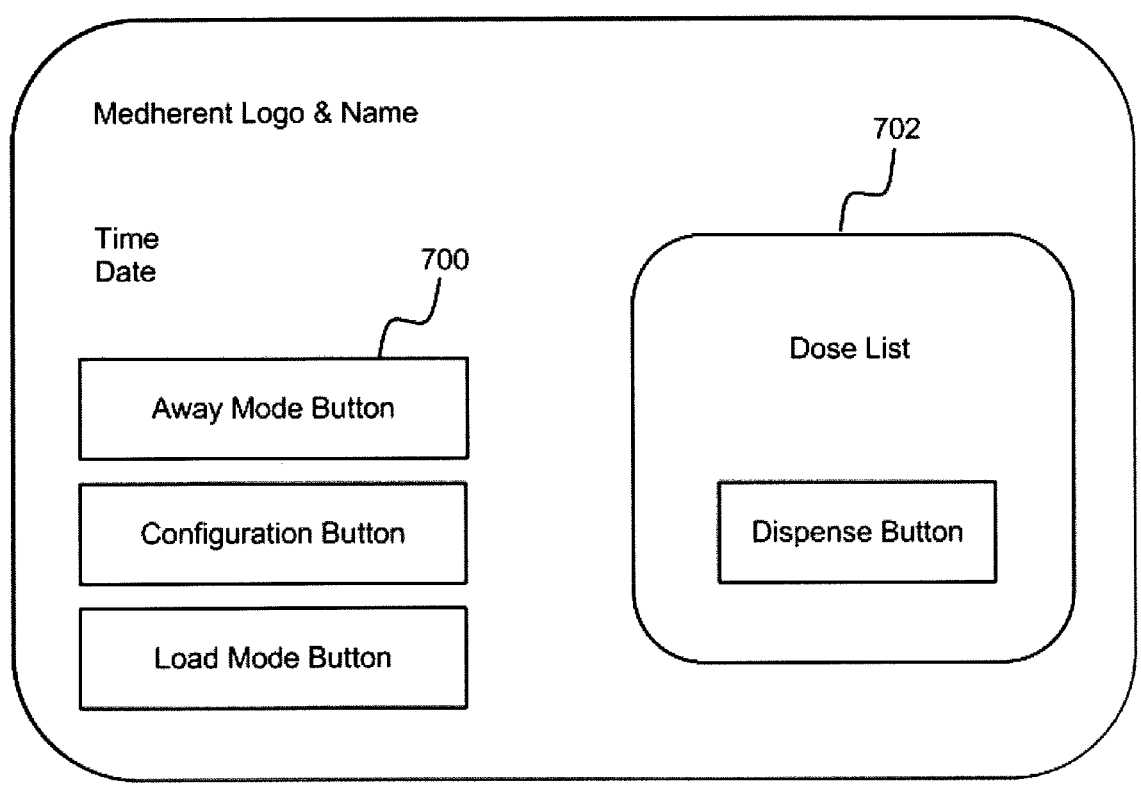

FIG. 20 represents the main vending controller user interface—main dosing screen.
  700: Navigation buttons (Away Mode, Configuration Mode, Load Mode).
  702: Dose schedule list. Displays time and status.

Figure 21:
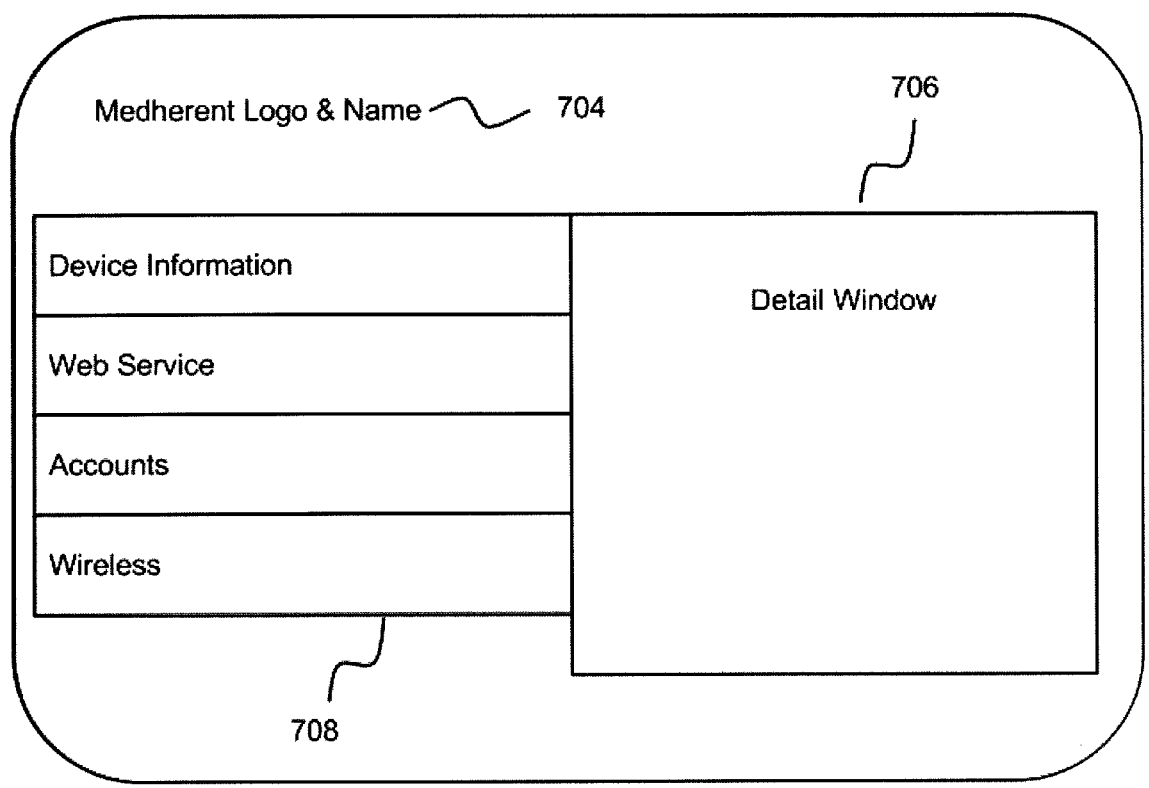

FIG. 21 represents the main vending controller user interface in configuration mode.
  704: Navigation button (Logo image button) back to main dosing screen.
  706: Detail window area (Right Pane) on the configuration screen.
  708: Configuration navigation list buttons (Left Pane) to access specific configuration settings.

Figure 22:
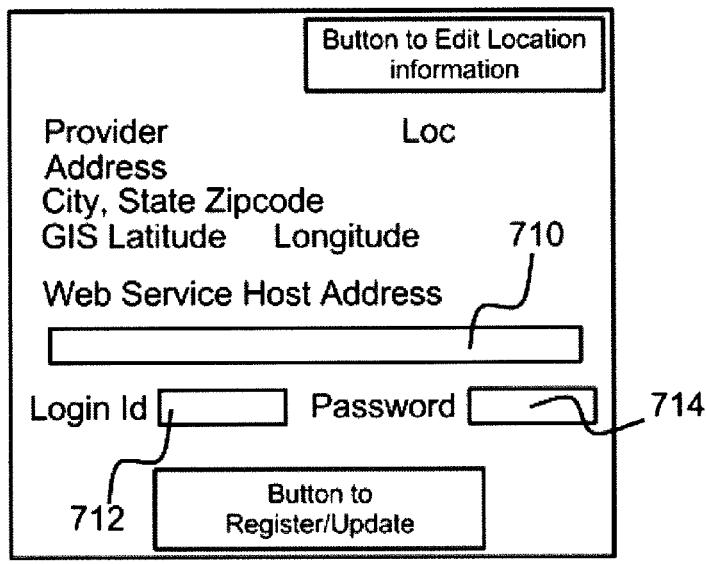

FIG. 22 represents the main vending controller user interface in configuration mode where the web service is selected.

| 710 | Web Service Host Address | Text (100) |
| 712 | Login Id | Text (20) |
| 714 | Password | Text (20) |

Figure 23:
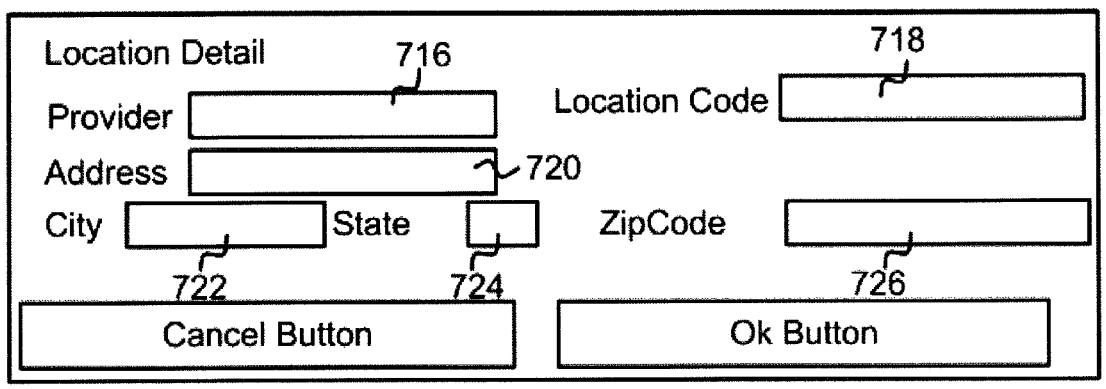

FIG. 23 represents the main vending controller user interface in configuration mode where the web service is selected and the location detail edit button was tapped.

| 716 | Provider | Text (25) |
| 718 | Location Code | Text (25) |
| 720 | Street Address | Text (25) |
| 722 | City | Text (25) |
| 724 | State | Drop Down List |
| 726 | Zip Code | Text (5) |

Figure 24:
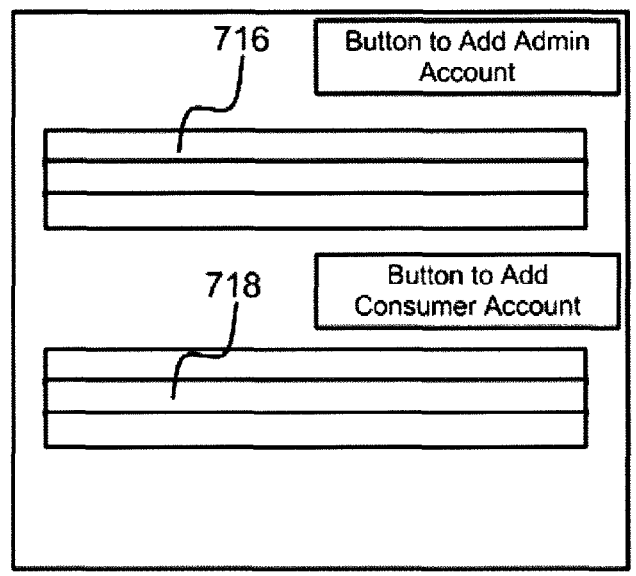

FIG. 24 represents the main vending controller user interface in configuration mode where the Accounts is selected
  716: List of administrator accounts. Tapping on a particular list item opens the dialog in edit mode.
  718: List of consumer accounts. Tapping on a particular list item opens the dialog in edit mode.

Figure 25:
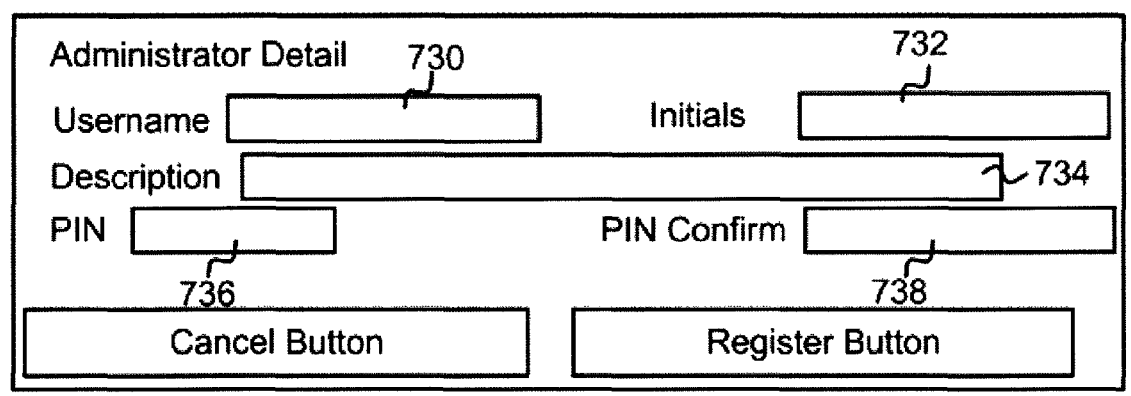

FIG. 25 represents the main vending controller user interface in configuration mode where Accounts is selected and the new administrator button is tapped.

| 730 | Medsupport Username | Text (15) |
| 732 | Medsupport User Initials | Text (4) |
| 734 | Description | Text (30) |
| 736 | PIN | Text (15) |
| 738 | Confirm PIN | Text (15) |

FIG. 26 represents the main vending controller user interface in configuration mode where Accounts is tapped and an administrator account list item is tapped.

| 740 | Description | Text (30) |
| 742 | Current PIN | Text (15) |
| 744 | New PIN | Text (15) |
| 746 | New PIN Confirm | Text (15) |

FIG. 27 represents the main vending controller user interface in configuration mode where Accounts is tapped and the new consumer button is tapped.

| 750 | Last Name | Text (15) |
| 752 | Last 4 digits of Social Security Number | Text (4) |
| 754 | Date of Birth | Long |
| 756 | Description | Text (30) |
| 758 | PIN | Text (15) |
| 760 | Confirm PIN | Text (15) |

Figure 28:
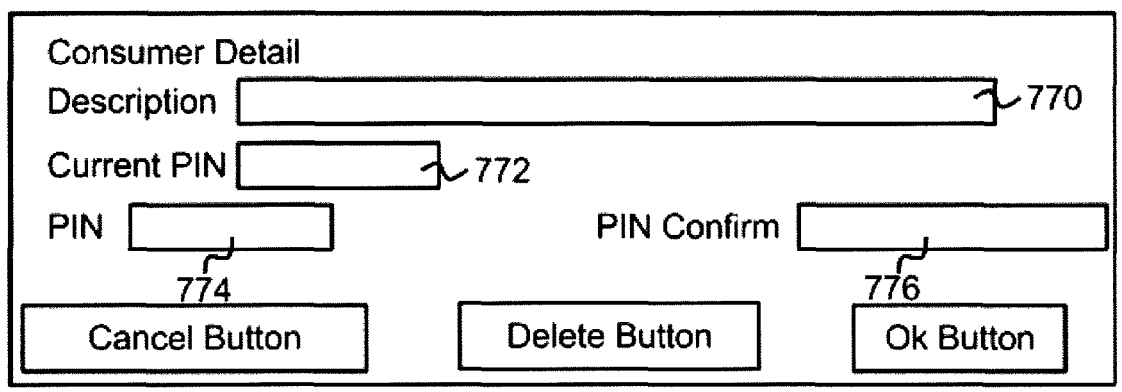

FIG. 28 represents the main vending controller user interface in configuration mode where the Account is selected and consumer account list item was tapped.

| 770 | Description | Text (30) |
| 772 | Current PIN | Text (15) |
| 774 | New PIN | Text (15) |
| 776 | Confirm New PIN | Text (15) |

Web Services

Figure 29:
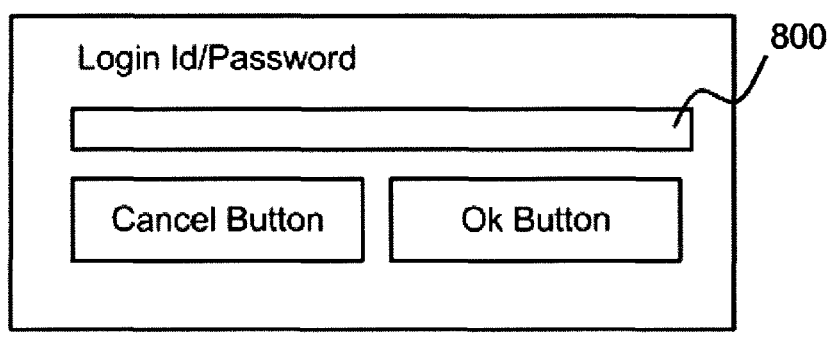

FIG. 29 represents the web services login dialog. Two pass login dialog.

| 800 | Login Id/Password | Text (30) |

Figure 30:
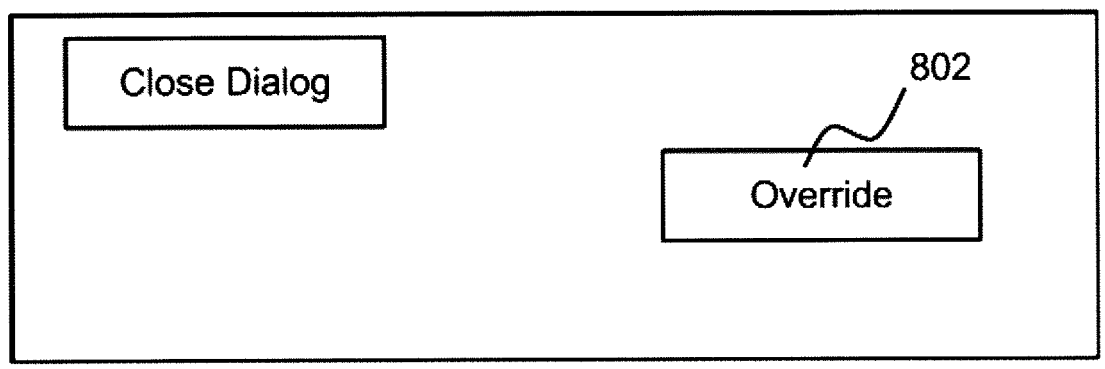

FIG. 30 represents the web services vending machine detail.
  802: Override button to get this particular vending machine out of Load Mode.

Figure 31:
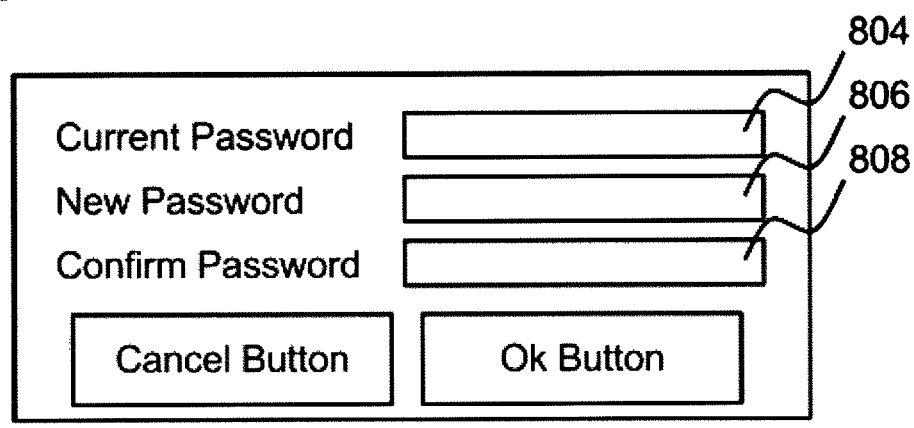

FIG. 31 represents the main vending controller user interface in configuration mode where the web service is selected.

| 804 | Current password | Text (30) |
| 806 | New password | Text (30) |
| 808 | Confirm new password | Text (30) |

Figure 32:
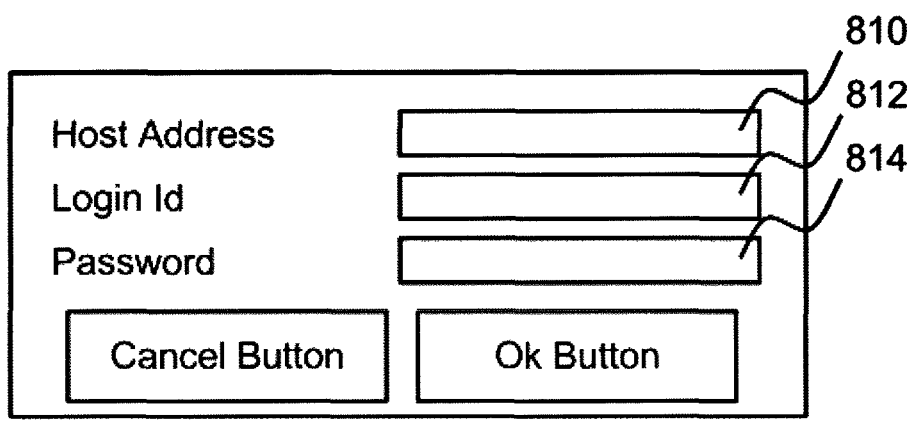

FIG. 32 represents the main vending controller user interface in configuration mode where the web service is selected.

| 810 | Web Service Host Address | Text (50) |
| 812 | Login Id | Text (30) |
| 814 | Password | Text (30) |

Example of Use

Scenario

A patient requires a combination of medications three times per day. The medications are packaged such that there are: morning, afternoon, and evening dose packets with the correct medications respectively packaged together for each dose time. This is equivalent to configuration c. in the listing of supported configurations above.

Implementation

Upon installation of the Medherent vending machine into the consumer's home, the vending controller tablet is started. Once the vending controller software has booted, the user will be required to configure the vending machine software so it knows where to look on the internet to communicate with the Medherent web service, and when to prompt for vending of medication packets. The user will tap the configuration button, enter the default PIN and proceed to input the vending machine location address, verify the web service host address and login credentials and finally, add administrator and consumer accounts.

The communication between the Medherent vending machine and the Medherent web services is performed over HTTP 1.1/SSL transport protocols using REST (Representational State Transfer) and XML entities. The web service resource expects login id and respective password headers to authenticate with the body entity containing the xml to process.

After the user enters the location information, and verifies the Medherent web service information, they will proceed to register the device with the Medherent web service. A successful registration will return the devices network Id, which will be stored locally. Once the device is registered with the Medherent web service, user accounts will need to be created.

The user will then create an Administrator account for the caregiver, which may also be the consumer. Regardless, at least one administrator account must exist. The user will then create a consumer account. Both of these accounts must be verified against the Medsupport web service, which maintains the patient eMAR. The Administrator account is verified by passing the MedSupport UserID to the Medsupport system. This is entered by the user setting up the vending controller. It is not stored locally, but sent up to the Medherent web service to be converted to HL7 and then passed to the MedSupport web service using an HL7 transaction:

Request Message to MedSupport
 MSH|^~\&|Medherent|{MachineNumber}|
CARASOLVA|{CompanyCode}|{DateTime
yyyyMMddhhmmss}||ADT^A01|{transaction number}||2.3|1|
 PID|1|{MedSupportLoginId}|{UserInitials}|||||
 PV1|1||{LocationCode}^^^{CompanyCode}|
MedSupport Acknowledgement Message
 MSH|^~\&|Carasolva|{MachineNumber}|Medherent|{CompanyCode}|{DateTime
yyyyMMddhhmmss}||ADT^O11|{transaction number}|ACK|2.3|1|
 MSA|{Response Code}|{Response text}|
 ERR|Error Code and Location|Error Location|HL7 Error Code||Severity|||||

The MedSupport web service will then POST a request containing the user Id of the MedSupport system. This information will be stored with the Medherent web service only. It will not flow to the vending machine. Rather, the Medherent web service will always communicate with the MedSupport web service and each vending machine using their respective local Ids.

The vending controller is then configured with the consumer's (patient's) dosing schedule by inputting patient information once, to link the vending machine to the patient's eMAR. The personally identifying information input at registration is not stored in the vending machine anywhere. Only numbers are used to identify the patient after the registration process is over, reducing the possibility of leaking patient data. Once linked, the dosing schedule is retrieved using the HL7 specification and an intermediate web service to translate the HL7 transaction into the vending controller's native structure:

Request Message to MedSupport
 MSH|^~\&|Medherent|{MachineNumber}|
CARASOLVA|{CompanyCode}|{DateTime
yyyyMMddhhmmss}||ADT^A01|{transaction number}||2.3|1|
 PID|1||||LastName|DOB||||||||||||SSN|
 PV1|1||{LocationCode}^^^{CompanyCode}|
MedSupport Acknowledgement Message
 MSH|^~\&|Carasolva|{MachineNumber}|Medherent|{CompanyCode}|{DateTime
yyyyMMddhhmmss}||ADT^O11|{transaction number}|ACK|2.3|
 MSA|{Response Code}|{Response text}|
 ERR|Error Code and Location|Error Location|HL7 Error Code||Severity|||||

The MedSupport web service will then POST a request containing the schedule of the patient:
MedSupport Response Message
 MSH|^~\&|Carasolva|CMS|Medherent|CompanyCode|DateTimeTransactionSent||RDE^O01|TransactionNumberFromRegisterTransaction|P|2.5|||||ASCII
 PID|1||MedsupportConsumerId|LastName||DateOfBirth|||||||||SSN4digits|
 PV1|1|I LocationCode^^^CompanyCodeGoe|
 TQ1|1|||DoseTimes|
Medherent Acknowledgement Message
 MSH|^~\&|Medherent|MH|Carasolva|CompanyCode GoesHere|DateTimeTransactionSent||RDE
^O13|TransactionNumber|P|2.5|||||ASCII|||
 MSA|Message Control ID|TransactionNumberFromRegisterTransaction|

The Medherent web service will then respond with the translated dosing schedule into Medherent xml entities, which are saved into the local Medherent vending machine database.

Figure 41:
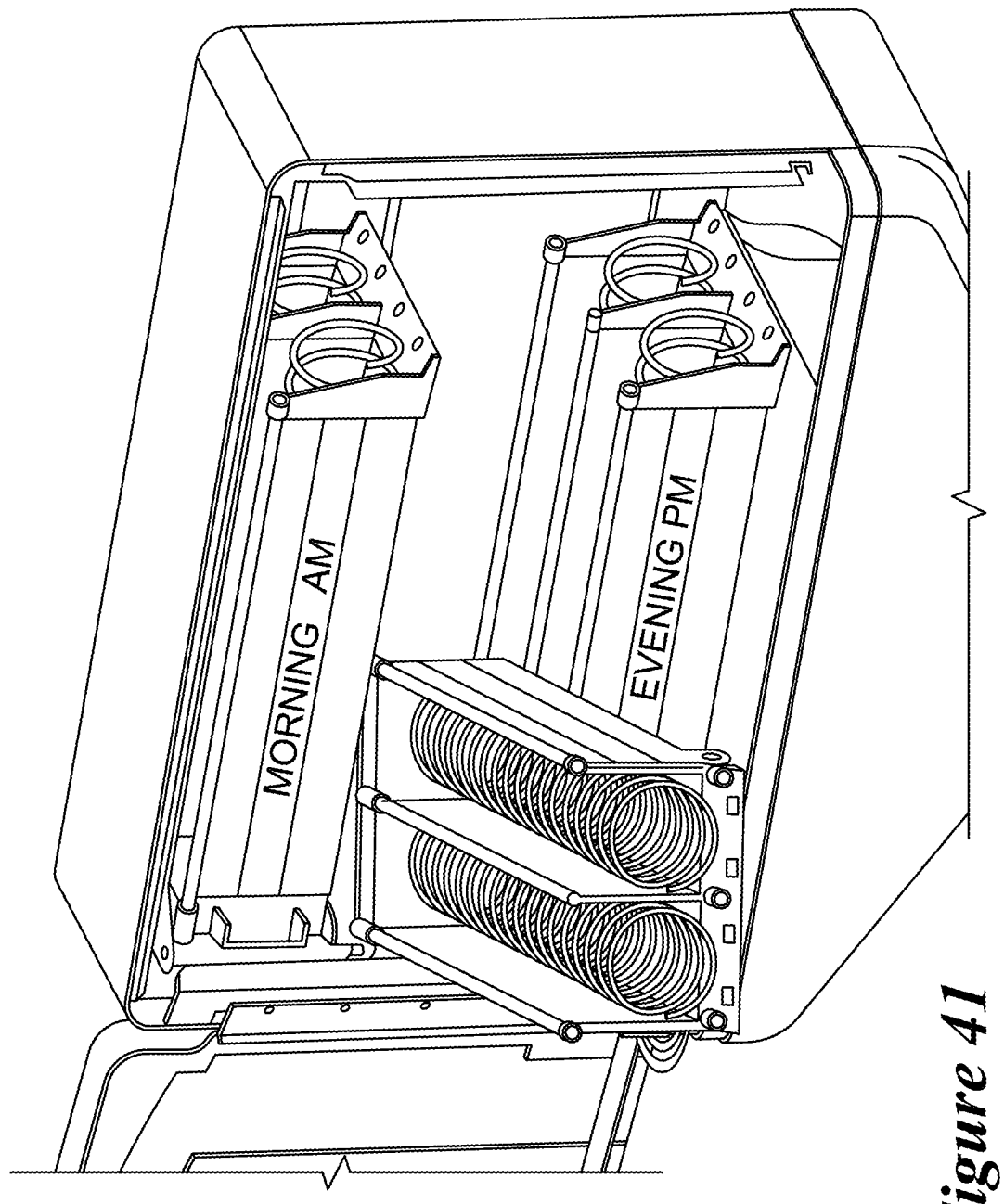

The pharmacy technician will then proceed to load the medication packets into the vending machine with respect to the configuration. In this example, the pharmacy technician fills the morning dose in tray 1 selections 1 & 2, the afternoon dose in tray 2 selections 1 & 2, and the evening dose in tray 3 selections 1 & 2. FIG. 41 shows a vending machine with tray 2 in a tray loading position. Once the door on the vending machine is closed, the technician must attest that they followed protocol when filling the vending machine and that the doses are in the correct tray selections. The vending machine will then go into dose mode.

Using the obtained dosing schedule, the vending machine queues the doses. When the time comes for a dose packet to be vended, the patient is alerted through visual and auditory prompts. The patient can vend the dose by tapping the dispense button and if required, entering their PIN (personal identification number). A short animation demonstrating how to open the packet is played during vending actuation.

When the patient vends a dose, the vending controller uses the configuration to determine the coil selection to actuate, then instructs the vending service to execute the vending operation. The vending service issues the following serial command over the USB cord tethered to the GVC board:

!SEL_LF where SEL represents the 3 digit selection number pertaining to the actuator address that is recognized by the GVC board.

When a dose packet is vended, the vending machine logs the event in the local database and transmits the dose vend event to the Medherent web service, where it is translated into an HL7 transaction, calls MedSupport web service updating the patient's eMAR.

Request Message to MedSupport

MSH|^~\&|Medherent|MH|Carasolva|CompanyCode|DateTimeTransactionSent||RDS^O13|TransactionNumber|P|2.5|||||ASCII|||

PID|1||MedSupportConsumerId|||||||||||||

RXD|1||Medpass datetime|MedherentConsumerId|

MedSupport Acknowledgement Message

MSH|^~\&|Carasolva|{MachineNumber}|Medherent|{CompanyCode}|{DateTime yyyyMMddhhmmss}||ADT^O11|{transaction number}|ACK|2.3|1|

MSA|{Response Code}|{Response text}|

ERR|Error Code and Location|Error Location|HL7 Error Code||Severity|||||

The vending machine then waits for the next dosing time where the process begins again.

Figure 33:
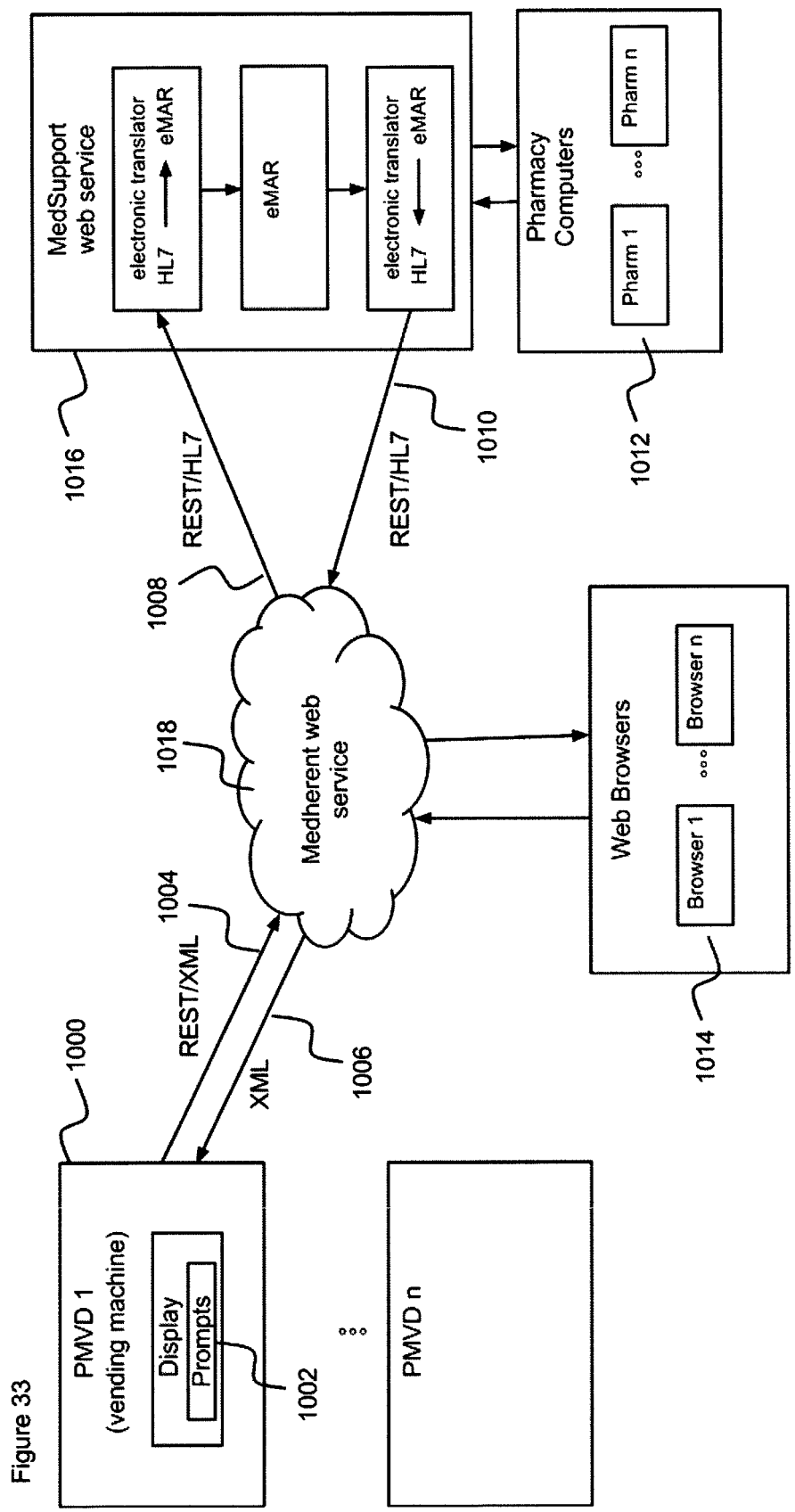
FIGS. 33 and 34 are schematic diagrams of system components of one preferred embodiment of the second implementation.

FIG. 33 represents an overview of the entire vending service, from vending machine, the Medherent web service, to the Medsupport web service which updates the eMAR.

- 1000: Prescription Medication Vending Device. This is where the medication will be stored, vended and the initiation of the update of the eMAR takes place. In the example, this device is what gets installed into the consumer's home.
- 1002: Tablet computer (see FIG. 51) displays information and prompts to the consumer and anyone interacting with the vending machine. This tablet per the example, is configured with user and scheduling information as well as information on how to connect to the Medherent web service. The tablet maintains the main data store locally.
- 1004: Local data collected either periodically or during events like the Medpass event in the example are communicated to the Medherent web service. The data are transmitted using HTTP/SSL with a REST POST, where the body entity of the request is the XML representation of the data. In the example, it includes registration data for linking the vending machine to the eMAR via administrator and consumer account registration.
- 1006: Responses from the server to: register a consumer, update the eMAR, obtain a schedule et. Al. are sent in the body entity of the response as the XML representation of the data. In the example: The Medherent web service will then respond with the translated dosing schedule into Medherent xml entities, which are saved into the local Medherent vending machine database.
- 1008: The Medherent web services, upon receiving a request from a vending machine as appropriate, translate the request from the vending machine into an HL7 transaction, append it to a new request that is POSTed to the Medsupport web service. In the example, the registration of a user as well as Medpass events all get translated and POSTed to Medsupport.
- 1010: The Medsupport web service handles the POST from the Medherent web service, translates the HL7 transaction, takes appropriate action with respect to the type of transaction which includes the update of the eMAR, then responds with the respective acknowledgement. Additionally if necessary, as a POST request to the Medherent web service. In the example, this would be Medsupport administrator, and consumer Ids and the consumer's dosing schedule.
- 1012: The pharmacy computers maintain the pharmacy record and originate medication schedules to the eMAR. The example would be the scenario that is illustrated.
- 1014: The Medherent web services, in addition to routing, also provide command and control features for the individual vending machines. The web services therefore provide a web user interface for such purposes. This is outside the scope of the example.
- 1016: The Medsupport web services provide features for translating vending events into updates to the eMAR.
- 1018: The Medherent web service sits in between the vending machine and the eMAR. To manage the amount of data transmitted over the air, the HL7 transaction protocol is translated into more efficient XML representations of the vending data necessary to implement the PMVD concept.

Figure 34:
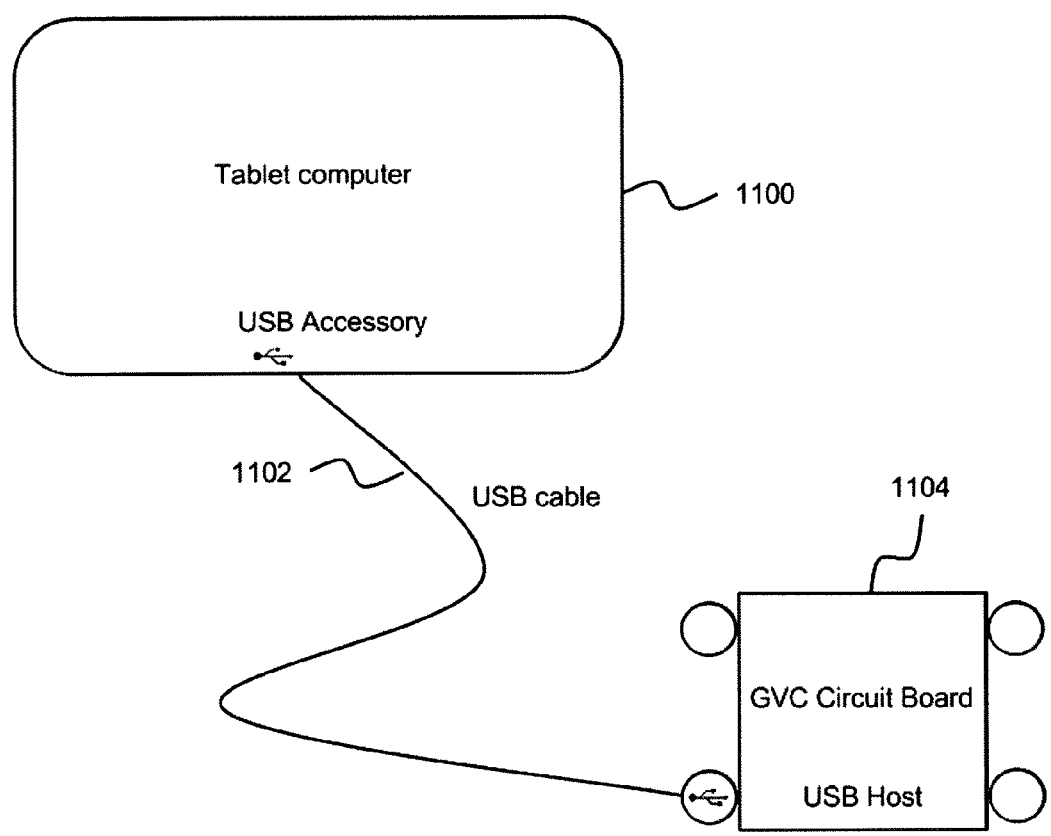

FIG. 34 represents the relationship between the tablet computer and the GVC (General Vending Controller) circuit board.

- 1100: The tablet computer is mounted such that the screen is flush with the front panel surface of the vending machine, seated in a cutout with brackets, and secured by a bezel whose mounting hardware is access from inside the vending machine. The screen, sound ports, as well as the power button and volume rockers are made accessible, while everything else on the tablet including but not limited to the USB port, remains inaccessible to the user inside the vending machine box.
- 1102: USB cable used to feed power to the tablet and transmit and receive serial commands to and from the GVC circuit board. This internal vending machine cable physically connects the tablet to the GVC board.
- 1104: The GVC board, also located inside the vending machine, is the main vending controller board which handles all serial commands from the tablet computer. Per the example, the tablet computer sends a serial command to the GVC board in the form of the literal '!011_LF' where 011 represents a physical motor address. This command is then handled by the GVC board and in turn actuates the motor in the selection row 1, column 1. If the vend happens, the GVC board replies to the tablet with a successful vend event, which propagates through the system resulting in a Medpass event in the eMAR.

Overview of the Medsupport Process Flow

Figure 35:
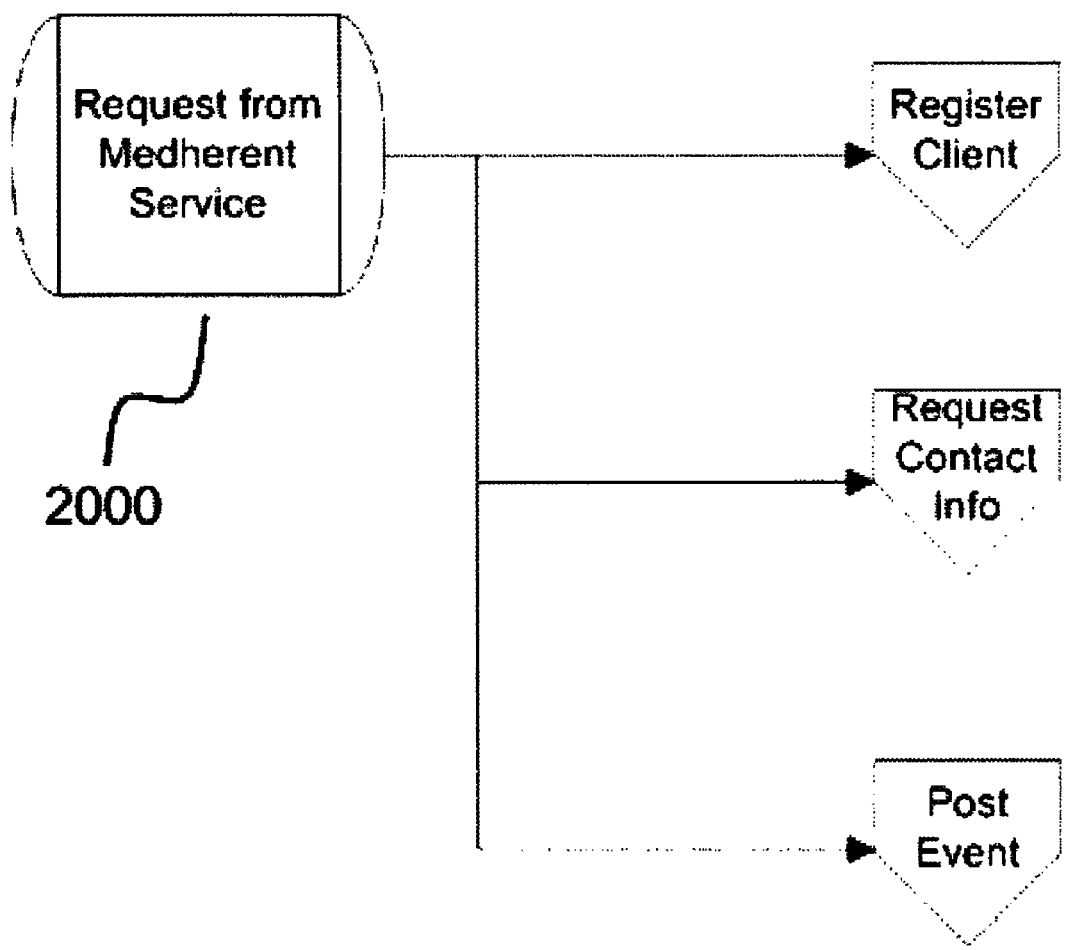
FIGS. 35-38 show flowcharts of MedSupport web service processes for use in one preferred embodiment of the second implementation.

FIG. 35 represents the Medsupport web service overview.

- 2000: Prescription Medication Vending Device. This is where the medication will be stored, vended and the initiation of the update of the eMAR takes place. In the example, this device is what gets installed into the consumer's home.

Figure 36:
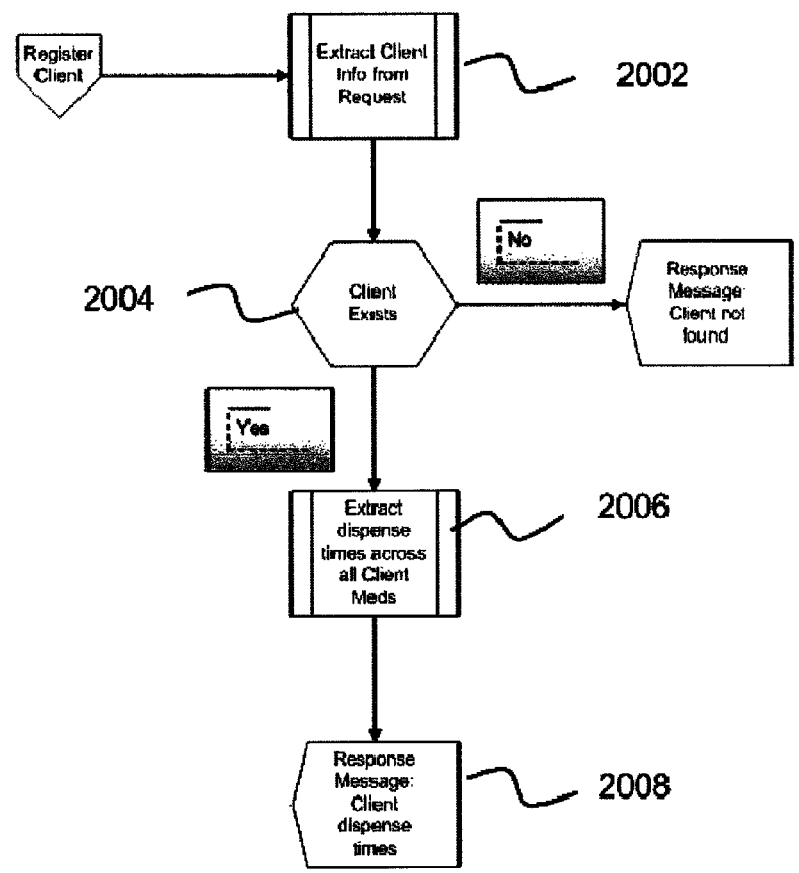

FIG. 36 represents the Medsupport web service client registration process. This process links the vending machine (PMVD) to the eMAR.

- 2002: The client information is parsed from the HL7 transaction and used to populate the local system entities.

2004: The eMAR is consulted with respect to consumer registrations to determine when linking to a particular vending machine this consumer's validity.

2006: If the consumer is valid the eMAR is consulted to obtain the consumer's dosing schedule.

2008: If there is a valid dosing schedule, it is returned in an HL7 formatted transaction POSTed to the Medherent web services along with the Medsupport UserId.

Figure 37:
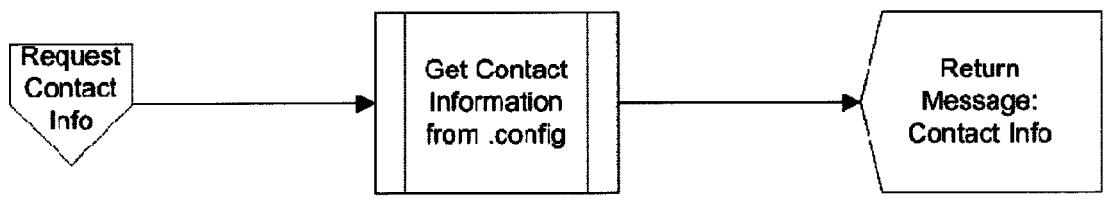

FIG. 37 represents the Medherent and Medsupport web services exchanging contact information.

Figure 38:
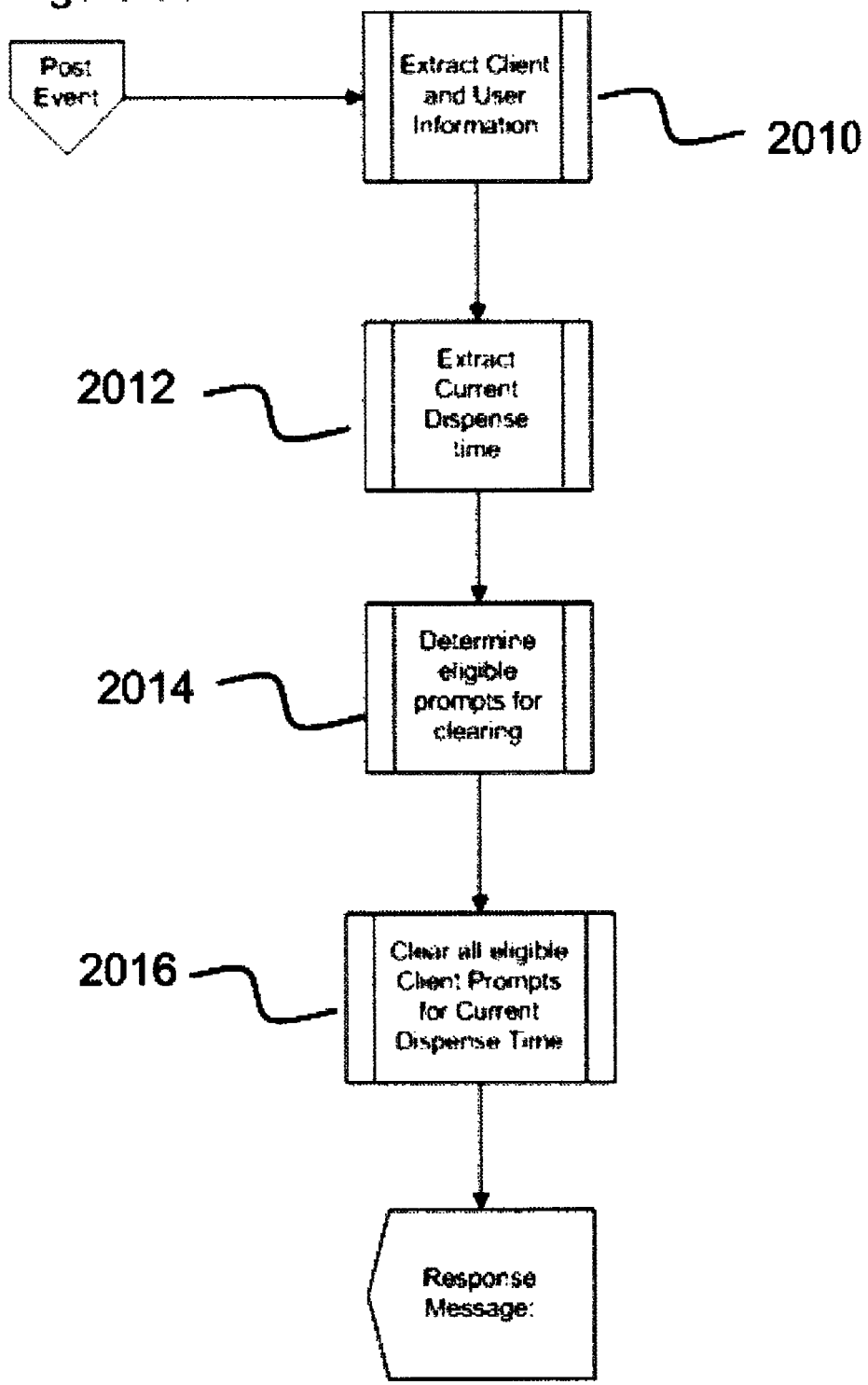

FIG. 38 represents the Medsupport web services receiving and processing a Medpass event.

2010: The client information is parsed from the HL7 transaction and used to populate the local system entities.

2012: The Medpass information is parsed from the HL7 transaction and used to populate the local system entities.

FIG. 39 represents 2 eMARs before and after the process in FIG. 55.

2014: Update the respective eMAR. In the example, patient 456 has their meds vended for the 7 AM dosing (the event that is represented in the previous process POST flow), but patient 123 has not yet vended their 8 AM dose, which is ready to be vended. FIG. 52 represents the two respective eMARs before patient 456's vending and after the event is POSTed to Medsupport via Medherent web services.

2016: Update Medsupport UI and respective system messages.

Referring again to the Example above, the following additional details are provided to further explain how a vending event is used to populate the eMAR with data.

Upon detection of a vending event, the vending machine communicates at least the following information to Medherent web services:

1. Patient ID (Patient Identification Segment (PID))
2. Scheduled dose time
3. Actual time of vending (optional)

Medherent web services maintains a Patient Medication Table (table) that contains the data fields shown in FIG. 43. Upon receipt of the information above, a check is made to identify whether there is a Patient ID and scheduled dose time that matches the incoming information. If so, the appropriate entry is made in the table indicating that the medications for that patient were vended, and thus, presumed to have been taken. The actual time of vending may be used for more granular compliance monitoring.

In IMPLEMENTATION 2, no prompts are sent to the vending machines from the Medherent web services since the vending machine has already been pre-programmed to generate its own prompts in accordance with the dose schedule. However, the table knows the time of prompts and uses this information as described above to identify a vending event for the patients being monitored in the eMAR.

Furthermore, in IMPLEMENTATION 2, no patient personalized information or medication details are communicated to Medherent web services. Thus, if the communicated information was intercepted by an unauthorized entity, the information could not be used to readily identify the patient or any of the medications that the patient has taken. Even if the unauthorized entity was able to determine the actual patient name from the Patient ID by gaining access to medical records other than the eMAR, the unauthorized entity would still not be able to determine what medications the patient has taken.

In an alternative embodiment, the vending machine communicates only the Patient ID to Medherent web services, without the scheduled dose time. In this embodiment, if the eMAR locates a record for the Patient ID, then it infers from the actual time what the scheduled dose time should be, and uses that information to complete the same process described above. For example, if the vending event is detected at 8:02 am and there is a scheduled dose time at 8:00 am, and no other scheduled dose time near 8:00 am, then it can be inferred that the scheduled dose time is 8:00 am.

In another alternative embodiment, a machine number of the vending machine or a static IP address of the tablet is sent in place of the Patient ID, and a translation table equivalent to database table 16 of FIG. 1 is used to identify the Patient ID. The process then proceeds as described in either of the embodiments above (i.e., with or without the scheduled dose time).

In addition, any unique identifier of the patient can be used in place of the patient ID used by the Medherent system. Again, a translation table would be required in this embodiment to obtain the Patient ID needed for the eMAR from the unique identifier.

The following specifications can be used for one preferred embodiment of hardware/software components. Any of the components can be substituted for different hardware/software having equivalent functionality.

| Hardware | |
| --- | --- |
| Form Factor | 7" touchscreen Android tablet: |
| Speakers | Integrated |
| Microphone | Integrated |
| Back-up battery | Integrated |
| Barcode reader | Optional |
| Orientation | Landscape |
| Connectivity | 3G Radio |
| | USB 2.0 H/S |
| | Wi-fi 802.11 a/b/g/n |
| | Bluetooth 3.0 |
| Camera | Front Camera: 2.0 Megapixel |
| | Rear Camera: 3.0 Megapixel Auto Focus with Flash |
| Core | CPU Processor Type - ARM11 |
| | CPU Processor Speed - 1.2 GHz |
| | Chipset - Qualcomm MSM7227 |
| Memory | Flash - 512 MB NAND Flash and micro SD expandability up to 32 GB Internal - 512 MB |
| Display | Type - 7" Capacitive multi-touch LCD screen with minimum 800x480 resolution |
| | Contrast Ratio 500:1 |
| | Brightness (nits) - 350 cd/m2 |
| Software | |
| Operating System | Android 4.0.4 (Ice Cream Sandwich) Stock |
| Service Controller | A background process that performs vending operations: Actuates 'dosing events' Respond to controller board events as necessary Communicates with physical hardware via the controller board |

| | |
|---|---|
| Main UI | Display overall system status |
| | System configuration UI link |
| | Away UI link |
| | Act on events to display information or prompts to user |
| | Display dosing information |
| | Status |
| | Allow user to identify themselves |
| Monitor Service | Monitor dispensary physical status |
| | Record metrics |
| | Hardware |
| | Software |
| | Data Usage |
| | Ensure all other components are operational |
| Reporting Service | Communicates with the Cloud Services |
| | Connect to the internet via wireless, WAN/LAN, cellular radio |
| | Reports to the Cloud Service |
| | Vending machine status |
| | Metrics |
| | Events |
| | Receives instructions from Cloud Service |
| | Receives dosing schedule from Cloud Service |
| | Sends/receives secure messages to/from Cloud Service |

All data will be transmitted over SSL connections.

Example of Transaction Segments

| Code | Text |
|---|---|
| RAR | PHARMACY ADMINISTRATION INFORMATION |
| RDR | PHARMACY DISPENSE INFORMATION |
| RER | PHARMACY, ENCODED ORDER INFORMATION |
| RES | RESULT |
| RGR | PHARMACY DOSE INFORMATION |
| ROR | PHARMACY PRESCRIPTION ORDER INFORMATION |
| RRA | PHARMACY ADMINISTRATION ACKNOWLEDGEMENT |
| RRD | PHARMACY DISPENSE ACKNOWLEDGEMENT |
| RDS | PHARMACY DISPENSE MESSAGE |
| RXD | PHARMACY DISPENSE |
| TQ | QUANTITY/TIMING |
| PV1 | PATIENT VISIT |
| PID | PATIENT IDENTIFICATION |
| MSH | MESSAGE READER |
| ER1 | ERROR |

Example of Acknowledgement Codes

| Code | Text |
|---|---|
| AA | APPLICATION ACCEPT |
| AE | APPLICATION ERROR |
| AR | APPLICATION REJECT |
| CA | COMMIT ACCEPT |
| CE | COMMIT ERROR |
| CR | COMMIT REJECT |

End of Details of Implementation 2

The present invention may be implemented with any combination of hardware and software. If implemented as a computer-implemented apparatus, the present invention is implemented using means for performing all of the steps and functions described above.

When implemented in software, the software code can be executed on any suitable processor or collection of processors, whether provided in a single computer or distributed among multiple computers.

The present invention can also be included in an article of manufacture (e.g., one or more computer program products) having, for instance, computer readable storage media. The storage media has computer readable program code stored therein that is encoded with instructions for execution by a processor for providing and facilitating the mechanisms of the present invention. The article of manufacture can be included as part of a computer system or sold separately.

The storage media can be any known media, such as computer memory, one or more floppy discs, compact discs, optical discs, magnetic tapes, flash memories, circuit configurations in Field Programmable Gate Arrays or other semiconductor devices, or other tangible computer storage medium. The storage media can be transportable, such that the program or programs stored thereon can be loaded onto one or more different computers or other processors to implement various aspects of the present invention as discussed above.

The computer(s) used herein may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable, mobile, or fixed electronic device.

The computer(s) may have one or more input and output devices. These devices can be used, among other things, to present a user interface. Examples of output devices that can be used to provide a user interface include printers or display screens for visual presentation of output and speakers or other sound generating devices for audible presentation of output.

Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems (e.g., Microsoft Windows® or Android®) or platforms. Additionally, such software may be written using any of a number of suitable programming languages and/or programming or scripting tools, and also may be compiled as executable machine language code or intermediate code that is executed on a framework or virtual machine.

The terms "program" or "software" are used herein in a generic sense to refer to any type of computer code or set of computer-executable instructions that can be employed to program a computer or other processor to implement various aspects of the present invention as discussed above. The computer program need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, and the like, that perform particular tasks or implement particular abstract data types. The functionality of the program modules may be combined or distributed as desired in various embodiments.

Data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Preferred embodiments of the present invention may be implemented as methods, of which examples have been provided. The acts performed as part of the methods may be ordered in any suitable way. Accordingly, embodiments may be constructed in which acts are performed in an order different than illustrated, which may include performing some acts simultaneously, even though such acts are shown as being sequentially performed in illustrative embodiments.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. A system for vending medication to a plurality of patients, the system comprising:
   (a) an electronic medication administration record (e-MAR) that includes:
      (i) first unique patient identifying information for each of the plurality of patients, and
      (ii) dosing schedules for each of the plurality of patients;
   (b) a plurality of vending medication devices remotely located from the e-MAR, each vending medication device being associated with one of the patients, each vending medication device including:
      (i) a database that maintains the dosing schedule for the patient associated with the respective vending medication device, and
      (ii) a controller configured to obtain and configure the dosing schedule for the associated patient before the medication is loaded into the vending medication device by:
         (A) electronically communicating second unique patient identifying information to the e-MAR, wherein the dosing schedule for the patient is located and retrieved from the e-MAR using the first and second unique patient identifying information and is electronically communicated to the controller, and
         (B) electronically storing the dosing schedule received from the e-MAR in the database of the vending medication device,
      wherein the controller is further configured to:
         (C) enter a dose mode to allow for vending of medication after the medication is loaded into the vending medication device in accordance with the previously configured dosing schedule, and
         (D) prompt the patient regarding when to take the medication based on the previously configured dosing schedule without receiving any instructions to do so from any external source at the time when a dose of medication should be taken based on the previously configured dosing schedule,
      wherein the controller configures the dosing schedule without any interaction with identifier information associated with or on medication packages.

2. The system of claim 1 wherein the e-MAR further includes:
   (iii) a record of vended medications for each of the patients, and
   wherein the controller is further configured to:
      (E) record each vending event and electronically communicate each vending event to the e-MAR for recordation of vended medication that matches the dosing schedule for the patient associated with the vending medication device.

3. The system of claim 2 wherein the medication is vended in multi-unit dose packages (MUDPs), and the e-MAR includes for each patient the contents of each MUDP to be vended at an appropriate dose time in the dosing schedule, and wherein a single vending event causes the e-MAR to record that a plurality of medications that make up the contents of the MUDP were vended.

4. The system of claim 1 wherein each vending medication device further includes:
   (iii) a plurality of vending locations, each vending location holding a medication package to be vended, and
   wherein the controller is further configured to vend the medication packages from a predefined vending location without receiving any instructions regarding the predefined vending location from any external source at the time of the vending event.

5. The system of claim 4 wherein the plurality of vending locations are in vending slots or columns.

6. The system of claim 1 wherein the controller is configured to perform steps (A) and (B) each time that medication is loaded into the vending medication device, thereby ensuring that the current dosing schedule maintained in the e-MAR becomes stored in the database and is used in a subsequent dose mode for patient prompting.

7. The system of claim 1 wherein the first and second unique patient identifying information are the same unique identifying information.

8. The system of claim 1 wherein the second unique patient identifying information is a machine number of the vending medication device or a static IP address associated with the vending medication device, and the system further comprises:

(c) a database table of (i) the second unique patient identifying information, and (ii) the first unique patient identifying information for use in locating patient records in the e-MAR associated with respective vending medication devices.

* * * * *